US012668794B2

(12) United States Patent
Gagnon et al.

(10) Patent No.: US 12,668,794 B2
(45) Date of Patent: Jun. 30, 2026

(54) ANTI-CRISPR NUCLEIC ACID INHIBITORS OF CRISPR-CAS EFFECTOR ENZYMES

(71) Applicants: Board of Trustees of Southern Illinois University, Carbondale, IL (US); The Royal Institution for the Advancement of Learning/McGill University, Montreal (CA)

(72) Inventors: Keith T. Gagnon, Carbondale, IL (US); Masad Damha, Montreal (CA); Christopher Barkau, Carbondale, IL (US); Daniel O'Reilly, Barnham (GB)

(73) Assignees: Board of Trustees of Southern Illinois University, Carbondale, IL (US); The Royal Institution for the Advancement of Learning/McGill University, Montreal (CA)

( * ) Notice: Subject to any disclaimer, the term of this patent is extended or adjusted under 35 U.S.C. 154(b) by 1160 days.

(21) Appl. No.: 17/280,994

(22) PCT Filed: Sep. 30, 2019

(86) PCT No.: PCT/US2019/053891
§ 371 (c)(1),
(2) Date: Mar. 29, 2021

(87) PCT Pub. No.: WO2020/069524
PCT Pub. Date: Apr. 2, 2020

(65) Prior Publication Data
US 2021/0355488 A1 Nov. 18, 2021

Related U.S. Application Data

(60) Provisional application No. 62/738,472, filed on Sep. 28, 2018.

(51) Int. Cl.
*C12N 15/11* (2006.01)
*C12N 9/22* (2006.01)

(52) U.S. Cl.
CPC ............... *C12N 15/11* (2013.01); *C12N 9/22* (2013.01); *C12N 2310/20* (2017.05); *C12N 2310/322* (2013.01); *C12N 2310/3519* (2013.01)

(58) Field of Classification Search
CPC ............... C12N 15/11; C12N 2310/20; C12N 2310/113; C12N 2310/315; C12N 2310/322; C12N 2310/3519
See application file for complete search history.

(56) References Cited

U.S. PATENT DOCUMENTS

| | | | | |
|---|---|---|---|---|
| 8,697,359 B1 * | 4/2014 | Zhang | ................... | C12N 15/907 |
| | | | | 435/6.13 |
| 2015/0232881 A1 | 8/2015 | Glucksmann et al. | | |
| 2020/0255836 A1 * | 8/2020 | Miyagishi | ............... | C12N 9/99 |

FOREIGN PATENT DOCUMENTS

| | | |
|---|---|---|
| WO | 2017160689 A1 | 9/2017 |
| WO | 2018085288 A1 | 5/2018 |
| WO | 2018093990 A1 | 5/2018 |

OTHER PUBLICATIONS

Maniv et al., CRISPR decoys Competitive inhibitors of CRISPR immunityRNA Biology 10(5): 694-699, 2013.*

(Continued)

*Primary Examiner* — Kevin K Hill
(74) *Attorney, Agent, or Firm* — Husch Blackwell LLP

(57) ABSTRACT

A CRISPR inhibitor molecule is provided, comprising an artificial nucleic acid construct having a first polynucleotide, the inhibitor molecule capable of establishing several points of contact with a CRISPR protein and high binding affinity thereto, is provided. The first polynucleotide may comprise a sequence selected from the group consisting of: a poly- (Continued)

nucleotide that interacts with a protospacer adjacent motif (PAM)-interaction (PI) domain of a CRISPR-associated (Cas) protein, a polynucleotide that interacts with a guide sequence of a crRNA or an equivalent position of a single-guide RNA, and a polynucleotide that interacts with a repeat region of a tracrRNA or an equivalent position of a single-guide RNA. The CRISPR inhibitor molecule may also comprise a second polynucleotide and a linker. Methods of using the CRISPR inhibitor molecule in therapeutic agent selection and creation, as well as part of a therapeutic treatment, are also provided.

11 Claims, 9 Drawing Sheets

Specification includes a Sequence Listing.

(56)                    References Cited

OTHER PUBLICATIONS www.calculator.net; last visited Aug. 6, 2024.*

Tang et al., Aptazyme-embedded guide RNAs enable ligand-responsive genome editing and transcriptional activation, Nature Comm. 8: Article 15939, doi: 10.1038/ncomms15939; available online Jun. 28, 2017.*

Carlson-Stevermer et al., Assembly of CRISPR ribonucleoproteins with biotinylated oligonucleotides via an RNA aptamer for precise gene editing, Nature Comm. 18: Article 1711, 13 pages, doi: 10.1038/s41467-017-01875-9; available online Nov. 23, 2017.*

Li et al., Synthetic Oligonucleotides Inhibit CRISPR-Cpf1-Mediated Genome Editing, Cell Reports 25: 3262-3272, available Dec. 18, 2018.*

Cho et al., Quantitative selection and parallel characterization of aptamers, PNAS 110(46): 18460-18465, 2013.* www.calculator.net/exponent caculator; last visited May 7, 2025.*

Anders C & Jinek M, In Vitro Enzymology of Cas9, Methods in Enzymology, 2014, pp. 1-20, vol. 546.

Barkau CL et al., Rationally Designed Anti-CRISPR Nucleic Acid Inhibitors of CRISPR-Cas9, Nucleic Acid Therapeutics, 2019, pp. 136-147, vol. 29, No. 3.

Basgall EM et al., Gene Drive Inhibition by the Anti-CRISPR Proteins AcrIIA2 and AcrIIA4 in *Saccharomyces cerevisiae*, Microbiology, 2018, pp. 464-474, vol. 164, No. 4.

Beaudet A & Meng L, Gene-Targeting Pharmaceuticals for Single-Gene Disorders, Human Molecular Genetics, 2016, pp. R18-R26, vol. 25, No. R1.

Bondy-Denomy J et al., Bacteriophage Genes that Inactivate the CRISPR/Cas Bacterial Immune System, Nature, 2013, pp. 429-432, vol. 493, No. 7432.

Bonetti D et al., Processing of DNA Ends in the Maintenance of Genome Stability, Frontiers in Genetics, 2018, article No. 390, vol. 9.

Champer J et al., Molecular Safeguarding of CRISPR Gene Drive Experiments, Elife, 2019, article No. e41439, vol. 8.

Chen JS et al., CRISPR-Cas12a Target Binding Unleashes Indiscriminate Single-Stranded DNase Activity, Science, 2018, pp. 436-439, vol. 360, No. 6387.

Chew WL, Immunity to CRISPR Cas9 and Cas12a Therapeutics, Wiley Interdisciplinary Reviews Systems Biology and Medicine , 2018, article number e1408, vol. 10, No. 1.

Cong L et al., Multiplex Genome Engineering Using CRISPR/Cas Systems, Science, 2013, pp. 819-823, vol. 339, No. 6121.

Corey DR, Nusinersen, an Antisense Oligonucleotide Drug for Spinal Muscular Atrophy, Nature Neuroscience, 2017, pp. 497-499, vol. 20, No. 4.

Cowley LL & Lam CR, The Neutralization of Heparin by Protamine, Surgery, 1948, pp. 97-99, vol. 24, No. 1.

Crudele JM & Chamberlain JS, Cas9 Immunity Creates Challenges for CRISPR Gene Editing Therapies, Nature Communications, 2018, article No. 3497, vol. 9, No. 1.

Dai W-J et al., CRISPR-Cas9 for in Vivo Gene Therapy: Promise and Hurdles, Molecular Therapy—Nucleic Acids, 2016, article No. e349, vol. 5, No. 8.

Deleavey GF & Damha MJ, Designing Chemically Modified Oligonucleotides for Targeted Gene Silencing, Chemistry & Biology, 2012, pp. 937-954, vol. 19, No. 8.

Doench JG et al., Optimized sgRNA Design to Maximize Activity and Minimize Off-Target Effects of CRISPR-Cas9, Nature Biotechnology, 2016, pp. 184-191, vol. 34, No. 2.

Dong D et al., Structural Basis of CRISPR-SpyCas9 Inhibition by an Anti-CRISPR Protein, Nature, 2017, pp. 436-439, vol. 546, No. 7658.

Eckstein F, Phosphorothioates, Essential Components of Therapeutic Oligonucleotides, Nucleic Acid Therapeutics, 2014, pp. 374-387, vol. 24, No. 6.

Fellmann C et al., Cornerstones of CRISPR-Cas in Drug Discovery and Therapy, Nature Reviews Drug Discovery, 2017, pp. 89-100, vol. 16, No. 2.

Gagnon KT & Corey DR, Stepping Toward Therapeutic CRISPR, Proceedings of the National Academy of Sciences of the United States of America, 2015, pp. 15536-15537, vol. 112, No. 51.

Gasiunas G et al., Cas9-crRNA Ribonucleoprotein Complex Mediates Specific DNA Cleavage for Adaptive Immunity in Bacteria, Proceedings of the National Academy of Sciences of the United States of America, 2012, pp. E2579- E2586, vol. 109, No. 39.

Hynes Ro et al., Toward Responsible Human Genome Editing, JAMA, 2017, pp. 1829-1830, vol. 317, No. 18.

International Search Report and Written Opinion of the International Searching Authority, issued for International Application No. PCT/US2019/053891, mailed Jan. 17, 2020.

Jiang F & Doudna JA, CRISPR-Cas9 Structures and Mechanisms. Annual Review of Biophysics, 2017, pp. 505-529, vol. 46.

Jinek M et al., A Programmable Dual-RNA-Guided DNA Endonuclease in Adaptive Bacterial Immunity, Science, 2012, pp. 816-821, vol. 337, No. 6096.

Kartje ZJ et al., Chimeric Guides Probe and Enhance Cas9 Biochemical Activity, Biochemistry, 2018, pp. 3027-3031, vol. 57, No. 21.

Khvorova A & Watts JK, The Chemical Evolution of Oligonucleotide Therapies of Clinical Utility, Nature Biotechnology, 2017, pp. 238-248, vol. 35, No. 3.

Kleinstiver BP et al., High-Fidelity CRISPR-Cas9 Variants with Undetectable Genome-Wide Off-Targets, Nature, 2016, 490-495, vol. 529, No. 7587.

Komor AC et al., Programmable Editing of a Target Base in Genomic DNA Without Double-Stranded DNA Cleavage, Nature, 2016, pp. 420-424, vol. 533, No. 7603.

Koonin EV, Evolution of RNA- and DNA-Guided Antivirus Defense Systems in Prokaryotes and Eukaryotes: Common Ancestry vs Convergence, Biology Direct, 2017, article No. 5, vol. 12, No. 1.

Kortright KE et al., Phage Therapy: A Renewed Approach to Combat Antibiotic-Resistant Bacteria, Cell Host & Microbe, 2019, pp. 219-232, vol. 25, No. 2.

Kruger A et al., Molecular Modeling Applied to Nucleic Acid-Based Molecule Development, Biomolecules, 2018, article No. 83, vol. 8, No. 3.

Mali P et al., RNA-Guided Human Genome Engineering via Cas9, Science, 2013, pp. 823-826, vol. 339, No. 6121.

NCBI, GenBank Accession No. LC377574.1, "Cloning Vector pCDF-CRISPR-CasWT DNA", Mar. 31, 2018.

Nishimasu H et al., Crystal Structure of Cas9 in Complex with Guide RNA and Target DNA, Cell, 2014, pp. 935-949, vol. 156, No. 5.

Nunez JK et al., Chemical and Biophysical Modulation of Cas9 for Tunable Genome Engineering, ACS Chemical Biology, 2016, pp. 681-688, vol. 11, No. 3.

O'geen H et al., How Specific is CRISPR/Cas9 Really?, Current Opinion in Chemical Biology, 2015, pp. 72-78, vol. 29.

(56)     References Cited

OTHER PUBLICATIONS

O'geen H et al., A Genome-Wide Analysis of Cas9 Binding Specificity Using ChIP-seq and Targeted Sequence Capture, Nucleic Acids Research, 2015, pp. 3389-3404, vol. 43, No. 6.

O'reilly D et al., Extensive CRISPR RNA Modification Reveals Chemical Compatibility and Structure-Activity Requirements for Cas9 Biochemical Activity, Nucleic Acids Research, 2019, pp. 546-558, vol. 47, No. 2.

Palermo G et al., CRISPR-Cas9 Conformational Activation as Elucidated from Enhanced Molecular Simulations, Proceedings of the National Academy of Sciences of the United States of America, 2017, pp. 7260-7265, vol. 114, No. 28.

Patra A et al., 2'-Fluoro RNA Shows Increased Watson-Crick H-Bonding Strength and Stacking Relative to RNA: Evidence from NMR and Thermodynamic Data, Angewandte Chemie (International Edition in English), 2012, pp. 11863-11866, vol. 51, No. 47.

Peng R et al., Potential Pitfalls of CRISPR/Cas9-Mediated Genome Editing, The FEBS Journal, 2016, pp. 1218-1231, vol. 283, No. 7.

Pineda M et al., Engineered CRISPR Systems for Next Generation Gene Therapies, ACS Synthetic Biology, 2017, pp. 1614-1626, vol. 6, No. 9.

Qi LS et al., Repurposing CRISPR as an RNA-Guided Platform for Sequence-Specific Control of Gene Expression, Cell, 2013, pp. 1173-1183, vol. 152, No. 5.

Rauch BJ et al., Inhibition of CRISPR-Cas9 with Bacteriophage Proteins, Cell, 2017, pp. 150-158, vol. 168, No. 1-2.

Richter F et al., Switchable Cas9, Current Opinion in Biotechnology, 2017, pp. 119-126, vol. 48.

Santos-Pereira JM & Aguilera A, R Loops: New Modulators of Genome Dynamics and Function, Nature Reviews Genetics, 2015, pp. 583-597, vol. 16, No. 10.

Schneider G, Automating Drug Discovery, Nature Reviews Drug Discovery, 2018, pp. 97-113, vol. 17, No. 2.

Shen X et al., Activating Frataxin Expression by Single-Stranded siRNAs Targeting the GAA Repeat Expansion, Bioorganic & Medicinal Chemistry Letters, 2018, pp. 2850-2855, vol. 28, No. 17.

Shin J et al., Disabling Cas9 by an Anti-CRISPR DNA Mimic, Science Advances, 2017, article No. e1701620, vol. 3.

Simhadri VL et al., Prevalence of Pre-Existing Antibodies to CRISPR-Associated Nuclease Cas9 in the USA Population, Molecular Therapy Methods & Clinical Development, 2018, pp. 105-112, vol. 10.

Sternberg SH et al., Conformational Control of DNA Target Cleavage by CRISPR-Cas9, Nature, 2015, pp. 110-113, vol. 527, No. 7576.

Stodola JL & Burgers PM, Mechanism of Lagging-Strand DNA Replication in Eukaryotes, Advances in Experimental Medicine and Biology, 2017, pp. 117-133, vol. 1042.

Tsai SQ et al., GUIDE-Seq Enables Genome-Wide Profiling of Off-Target Cleavage by CRISPR-Cas Nucleases, Nature Biotechnology, 2015, pp. 187-197, vol. 33, No. 2.

Wang S et al., No Off-Target Mutations in Functional Genome Regions of a CRISPR/Cas9-Generated Monkey Model of Muscular Dystrophy, The Journal of Biological Chemistry, 2018, pp. 11654-11658, vol. 293, No. 30.

Watters KE et al., Systematic Discovery of Natural CRISPR-Cas12a Inhibitors, Science, 2018, pp. 236-239, vol. 362, No. 6411.

Watts JK et al., Chemically Modified siRNA: Tools and Applications, Drug Discovery Today, 2008, pp. 842-855, vol. 13, No. 19-20.

Wiedenheft B et al., RNA-Guided Genetic Silencing Systems in Bacteria and Archaea, Nature, 2012, pp. 331-338, vol. 482, No. 7385.

Wilson RC & Gilbert LA, The Promise and Challenge of In Vivo Delivery for Genome Therapeutics, ACS Chemical Biology, 2018, pp. 376-382, vol. 13, No. 2.

Wood H, FDA Approves Patisiran to Treat Hereditary Transthyretin Amyloidosis, Nature Reviews Neurology, 2018, p. 570, vol. 14, No. 10.

Yasaka M et al., Correction of INR by Prothrombin Complex Concentrate and Vitamin K in Patients with Warfarin Related Hemorrhagic Complication, Thrombosis Research, 2002, pp. 25-30, vol. 108, No. 1.

Yin H et al., Partial DNA-Guided Cas9 Enables Genome Editing with Reduced Off-Target Activity, Nature Chemical Biology, 2018, pp. 311-316, vol. 14, No. 3.

Zhu Y et al., Structural Insights into the Inactivation of CRISPR-Cas Systems by Diverse Anti-CRISPR Proteins, BMC Biology, 2018, article No. 32, vol. 16.

* cited by examiner

| Name | Mods | Sequences (5'-3') | Mass calculated | Mass found | Length |
|---|---|---|---|---|---|
| Anti1_crEGIP SEQ ID NO: 7 | 2'-O-CH₃ RNA | CGG₅U₅GAACAGCUCCUCGC | 5991.10 | 5991.50 | 18 |
| Anti1_tracr SEQ ID NO: 3 | 2'-O-CH₃ RNA | UUA UUU UAA CUU GCU AU | 5510.60 | 5511.20 | 17 |
| Anti1_PAM SEQ ID NO: 2 | DNA | CCG TGG TAT TGG AAA CAA TAC CAC GG | 8004.20 | 8005.20 | 26 |
| Anti1_PAM-crEGIP SEQ ID NO: 8 | DNA-2'-O-CH₃ RNA | C₅CG TGG TAT TGG AAA CAA TAC CAC GG₅U₅ GAA CAG CUC CUC GC | 13065.70 | 13067.60 | 41 |
| Anti1_PAM-tracr SEQ ID NO: 9 | DNA-2'-O-CH₃ RNA | C₅CG TGG TAT TGG AAA CAA TAC CAC GG -(Hexa PEG)-AUU UUA ACU UGC UAU | 13296.80 | 13297.40 | 44 |
| Anti2_PAM-tracr SEQ ID NO: 11 | DNA-2'-O-CH₃ RNA | C₅CG TGG TAT TGG AAA CAA TAC CAC GG -(Hexa PEG)-GUU UUA GAG CUAUGC UGU | 14374.40 | 14375.80 | 44 |
| Anti2_PAM-tracr_RNA SEQ ID NO: 10 | DNA-RNA | C₅CG TGG TAT TGG AAA CAA TAC CAC GG -(Hexa PEG)-GUU UUA GAG CUAUGC UGU | 14121.90 | 14124.40 | 44 |
| antiCR1 SEQ ID NO: 12 | DNA-FRNA | C₅CG TGG TAT TGG AAA CAA TAC CAC GG -(Hexa PEG)-A*U*U* U*U*A* A*C*U* U*G*C* U*A*U* | 13116.36 | 13116.27 | 41 |
| antiCR2 SEQ ID NO: 13 | DNA-FRNA-LNA | C₅CG TGG TAT TGG AAA CAA TAC CAC GG -(Hexa PEG)-A*U*U* _T_U*A* _A_C*U* _T_G*C* U*A*U* | 13174.42 | 13174.03 | 41 |
| Anti1_PAM-tracr SEQ ID NO: 14 | DNA-2'-O-CH₃ RNA | C₅CG TGG TAT TGG AAA CAA TAC CAC GG -(Linker)-AUU UUA ACU UGC UAU | 13296.80 | 13297.40 | 44 |
| Anti2_PAM-tracr SEQ ID NO: 15 | DNA-2'-O-CH₃ RNA | C₅CG TGG TAT TGG AAA CAA TAC CAC GG -(Linker)-GUU UUA GAG CUAUGC UGU | 14374.40 | 14375.80 | 44 |
| Anti2_PAM-tracr_RNA SEQ ID NO: 16 | DNA-RNA | C₅CG TGG TAT TGG AAA CAA TAC CAC GG -(Linker)-GUU UUA GAG CUAUGC UGU | 14121.90 | 14124.40 | 44 |
| antiCR1 SEQ ID NO: 17 | DNA-FRNA | C₅CG TGG TAT TGG AAA CAA TAC CAC GG -(Linker)-A*U*U* U*U*A* A*C*U* U*G*C* U*A*U* | 13116.36 | 13116.27 | 41 |
| antiCR2 SEQ ID NO: 18 | DNA-FRNA-LNA | C₅CG TGG TAT TGG AAA CAA TAC CAC GG -(Linker)-A*U*U* _T_U*A* _A_C*U* _T_G*C* U*A*U* | 13174.42 | 13174.03 | 41 |

Legend:

DNA = Italics

2'-O-CH₃RNA = Bold and Underlined

RNA = Bold, No Italics, No underline

LNA = Italics and underline (_A_ , _T_)

FRNA* = a nucleotide that is 2'F (Examples, A*, U*, C*, G*)

Linker = a nucleotide linker, examples are 3 atom or 27 atoms polyethylene glycol linkers (an example is Hexa PEG);

ₛ=PS linker

FIG. 1A

SEQUENCE LISTING

```
<160> NUMBER OF SEQ ID NOS: 24

<210> SEQ ID NO 1
<211> LENGTH: 23
<212> TYPE: DNA
<213> ORGANISM: Artificial Sequence
<220> FEATURE:
<223> OTHER INFORMATION: Polynucleotide that Interacts with a PI Domain
      of a Cas Protein

<400> SEQUENCE: 1
ccgtggtatt ggaaacaata cca                                            23

<210> SEQ ID NO 2
<211> LENGTH: 26
<212> TYPE: DNA
<213> ORGANISM: Artificial Sequence
<220> FEATURE:
<223> OTHER INFORMATION: Polynucleotide that Interacts with a PI Domain
      of a Cas Protein

<400> SEQUENCE: 2
ccgtggtatt ggaaacaata ccacgg                                         26

<210> SEQ ID NO 3
<211> LENGTH: 17
<212> TYPE: RNA
<213> ORGANISM: Artificial Sequence
<220> FEATURE:
<223> OTHER INFORMATION: Polynucleotide that Interacts with a Repeat
      Region of a tracrRNA or an Equivalent Position of a Single-Guide
      RNA
```

-continued

```
<400> SEQUENCE: 3
uuauuuuaac uugcuau                                              17

<210> SEQ ID NO 4
<211> LENGTH: 15
<212> TYPE: RNA
<213> ORGANISM: Artificial Sequence
<220> FEATURE:
<223> OTHER INFORMATION: Polynucleotide that Interacts with a Repeat
      Region of a tracrRNA or an Equivalent Position of a Single-Guide
      RNA

<400> SEQUENCE: 4
auuuuaacuu gcuau                                                15

<210> SEQ ID NO 5
<211> LENGTH: 18
<212> TYPE: RNA
<213> ORGANISM: Artificial Sequence
<220> FEATURE:
<223> OTHER INFORMATION: Polynucleotide that Interacts with a Repeat
      Region of a tracrRNA or an Equivalent Position of a Single-Guide
      RNA

<400> SEQUENCE: 5
guuuuagagc uaugcugu                                             18

<210> SEQ ID NO 6
<211> LENGTH: 15
<212> TYPE: DNA
<213> ORGANISM: Artificial Sequence
<220> FEATURE:
<223> OTHER INFORMATION: Polynucleotide that Interacts with a Repeat
      Region of a tracrRNA or an Equivalent Position of a Single-Guide
      RNA
<220> FEATURE:
<221> NAME/KEY: modified_base
<222> LOCATION: (4)..(4)
<223> OTHER INFORMATION: Thymine
<220> FEATURE:
<221> NAME/KEY: modified_base
<222> LOCATION: (10)..(10)
<223> OTHER INFORMATION: Thymine

<400> SEQUENCE: 6
auutuaacut gcuau                                                15

<210> SEQ ID NO 7
<211> LENGTH: 18
<212> TYPE: RNA
<213> ORGANISM: Artificial Sequence
<220> FEATURE:
<223> OTHER INFORMATION: Polynucleotide that Interacts with a Guide
      Sequence of a crRNA or an Equivalent Position of a Single-Guide
      RNA

<400> SEQUENCE: 7
cggugaacag cuccucgc                                             18

<210> SEQ ID NO 8
<211> LENGTH: 41
<212> TYPE: DNA
<213> ORGANISM: Artificial Sequence
<220> FEATURE:
<223> OTHER INFORMATION: Anti1_PAM-crEGIP
<220> FEATURE:
<221> NAME/KEY: modified_base
<222> LOCATION: (1)..(2)
<223> OTHER INFORMATION: Phosphorothioate linkages
```

-continued

```
<220> FEATURE:
<221> NAME/KEY: misc_feature
<222> LOCATION: (1)..(23)
<223> OTHER INFORMATION: DNA
<220> FEATURE:
<221> NAME/KEY: misc_feature
<222> LOCATION: (24)..(41)
<223> OTHER INFORMATION: RNA
<220> FEATURE:
<221> NAME/KEY: modified_base
<222> LOCATION: (24)..(41)
<223> OTHER INFORMATION: 2-Prime-O-methyl ribonucleotides
<220> FEATURE:
<221> NAME/KEY: modified_base
<222> LOCATION: (26)..(28)
<223> OTHER INFORMATION: Phosphorothioate linkages

<400> SEQUENCE: 8
ccgtggtatt ggaaacaata ccacggugaa cagcuccucg c                    41

<210> SEQ ID NO 9
<211> LENGTH: 41
<212> TYPE: DNA
<213> ORGANISM: Artificial Sequence
<220> FEATURE:
<223> OTHER INFORMATION: Anti1 _PAM-tracr
<220> FEATURE:
<221> NAME/KEY: modified_base
<222> LOCATION: (1)..(2)
<223> OTHER INFORMATION: Phosphorothioate linkages
<220> FEATURE:
<221> NAME/KEY: misc_feature
<222> LOCATION: (1)..(26)
<223> OTHER INFORMATION: DNA
<220> FEATURE:
<221> NAME/KEY: misc_feature
<222> LOCATION: (27)..(41)
<223> OTHER INFORMATION: RNA
<220> FEATURE:
<221> NAME/KEY: modified_base
<222> LOCATION: (27)..(41)
<223> OTHER INFORMATION: 2-Prime-O-methyl ribonucleotides

<400> SEQUENCE: 9
ccgtggtatt ggaaacaata ccacggauuu uaacuugcua u                    41

<210> SEQ ID NO 10
<211> LENGTH: 44
<212> TYPE: DNA
<213> ORGANISM: Artificial Sequence
<220> FEATURE:
<223> OTHER INFORMATION: Anti2 _PAM-tracr_RNA
<220> FEATURE:
<221> NAME/KEY: misc_feature
<222> LOCATION: (1)..(26)
<223> OTHER INFORMATION: DNA
<220> FEATURE:
<221> NAME/KEY: modified_base
<222> LOCATION: (1)..(2)
<223> OTHER INFORMATION: Phosphorothioate linkages
<220> FEATURE:
<221> NAME/KEY: misc_feature
<222> LOCATION: (27)..(44)
<223> OTHER INFORMATION: RNA

<400> SEQUENCE: 10
ccgtggtatt ggaaacaata ccacggguuu uagagcuaug cugu                 44

<210> SEQ ID NO 11
<211> LENGTH: 44
<212> TYPE: DNA
<213> ORGANISM: Artificial Sequence
<220> FEATURE:
```

```
<223> OTHER INFORMATION: Anti2 _PAM-tracr
<220> FEATURE:
<221> NAME/KEY: modified_base
<222> LOCATION: (1)..(2)
<223> OTHER INFORMATION: Phosphorothioate linkages
<220> FEATURE:
<221> NAME/KEY: misc_feature
<222> LOCATION: (1)..(26)
<223> OTHER INFORMATION: DNA
<220> FEATURE:
<221> NAME/KEY: misc_feature
<222> LOCATION: (27)..(44)
<223> OTHER INFORMATION: RNA
<220> FEATURE:
<221> NAME/KEY: modified_base
<222> LOCATION: (27)..(44)
<223> OTHER INFORMATION: 2-Prime-O-methyl ribonucleotides

<400> SEQUENCE: 11
ccgtggtatt ggaaacaata ccacggguuu uagagcuaug cugu                          44

<210> SEQ ID NO 12
<211> LENGTH: 41
<212> TYPE: DNA
<213> ORGANISM: Artificial Sequence
<220> FEATURE:
<223> OTHER INFORMATION: antiCR1
<220> FEATURE:
<221> NAME/KEY: modified_base
<222> LOCATION: (1)..(2)
<223> OTHER INFORMATION: Phosphorothioate linkages
<220> FEATURE:
<221> NAME/KEY: misc_feature
<222> LOCATION: (1)..(26)
<223> OTHER INFORMATION: DNA
<220> FEATURE:
<221> NAME/KEY: misc_feature
<222> LOCATION: (27)..(41)
<223> OTHER INFORMATION: RNA
<220> FEATURE:
<221> NAME/KEY: modified_base
<222> LOCATION: (27)..(41)
<223> OTHER INFORMATION: 2-Prime-fluoro nucleotides

<400> SEQUENCE: 12
ccgtggtatt ggaaacaata ccacggauuu uaacuugcua u                            41

<210> SEQ ID NO 13
<211> LENGTH: 41
<212> TYPE: DNA
<213> ORGANISM: Artificial Sequence
<220> FEATURE:
<223> OTHER INFORMATION: antiCR2
<220> FEATURE:
<221> NAME/KEY: modified_base
<222> LOCATION: (1)..(2)
<223> OTHER INFORMATION: Phosphorothioate linkages
<220> FEATURE:
<221> NAME/KEY: misc_feature
<222> LOCATION: (1)..(26)
<223> OTHER INFORMATION: DNA
<220> FEATURE:
<221> NAME/KEY: misc_feature
<222> LOCATION: (27)..(41)
<223> OTHER INFORMATION: RNA
<220> FEATURE:
<221> NAME/KEY: modified_base
<222> LOCATION: (27)..(29)
<223> OTHER INFORMATION: 2-Prime-fluoro nucleotides
<220> FEATURE:
<221> NAME/KEY: modified_base
<222> LOCATION: (30)..(30)
<223> OTHER INFORMATION: Locked nucleic acid
<220> FEATURE:
<221> NAME/KEY: modified_base
```

```
<222> LOCATION: (31)..(32)
<223> OTHER INFORMATION: 2-Prime-fluoro nucleotides
<220> FEATURE:
<221> NAME/KEY: modified_base
<222> LOCATION: (33)..(33)
<223> OTHER INFORMATION: Locked nucleic acid
<220> FEATURE:
<221> NAME/KEY: modified_base
<222> LOCATION: (34)..(35)
<223> OTHER INFORMATION: 2-Prime-fluoro nucleotides
<220> FEATURE:
<221> NAME/KEY: modified_base
<222> LOCATION: (36)..(36)
<223> OTHER INFORMATION: Locked nucleic acid
<220> FEATURE:
<221> NAME/KEY: modified_base
<222> LOCATION: (37)..(41)
<223> OTHER INFORMATION: 2-Prime-fluoro nucleotides

<400> SEQUENCE: 13
ccgtggtatt ggaaacaata ccacggauut uaacutgcua u                          41

<210> SEQ ID NO 14
<211> LENGTH: 41
<212> TYPE: DNA
<213> ORGANISM: Artificial Sequence
<220> FEATURE:
<223> OTHER INFORMATION: Anti1 _PAM-tracr
<220> FEATURE:
<221> NAME/KEY: modified_base
<222> LOCATION: (1)..(2)
<223> OTHER INFORMATION: Phosphorothioate linkages
<220> FEATURE:
<221> NAME/KEY: misc_feature
<222> LOCATION: (1)..(26)
<223> OTHER INFORMATION: DNA
<220> FEATURE:
<221> NAME/KEY: misc_feature
<222> LOCATION: (27)..(41)
<223> OTHER INFORMATION: RNA
<220> FEATURE:
<221> NAME/KEY: modified_base
<222> LOCATION: (27)..(41)
<223> OTHER INFORMATION: 2-Prime-O-methyl ribonucleotides

<400> SEQUENCE: 14
ccgtggtatt ggaaacaata ccacggauuu uaacuugcua u                          41

<210> SEQ ID NO 15
<211> LENGTH: 44
<212> TYPE: DNA
<213> ORGANISM: Artificial Sequence
<220> FEATURE:
<223> OTHER INFORMATION: Anti2 _PAM-tracr
<220> FEATURE:
<221> NAME/KEY: misc_feature
<222> LOCATION: (1)..(26)
<223> OTHER INFORMATION: DNA
<220> FEATURE:
<221> NAME/KEY: modified_base
<222> LOCATION: (1)..(2)
<223> OTHER INFORMATION: Phosphorothioate linkages
<220> FEATURE:
<221> NAME/KEY: misc_feature
<222> LOCATION: (27)..(44)
<223> OTHER INFORMATION: RNA
<220> FEATURE:
<221> NAME/KEY: modified_base
<222> LOCATION: (27)..(44)
<223> OTHER INFORMATION: 2-Prime-O-methyl ribonucleotides

<400> SEQUENCE: 15
ccgtggtatt ggaaacaata ccacggguuu uagagcuaug cugu                       44
```

```
<210> SEQ ID NO 16
<211> LENGTH: 44
<212> TYPE: DNA
<213> ORGANISM: Artificial Sequence
<220> FEATURE:
<223> OTHER INFORMATION: Anti2 _PAM-tracr_RNA
<220> FEATURE:
<221> NAME/KEY: modified_base
<222> LOCATION: (1)..(2)
<223> OTHER INFORMATION: Phosphorothioate linkages
<220> FEATURE:
<221> NAME/KEY: misc_feature
<222> LOCATION: (1)..(26)
<223> OTHER INFORMATION: DNA
<220> FEATURE:
<221> NAME/KEY: misc_feature
<222> LOCATION: (27)..(44)
<223> OTHER INFORMATION: RNA

<400> SEQUENCE: 16
ccgtggtatt ggaaacaata ccacggguuu uagagcuaug cugu                          44

<210> SEQ ID NO 17
<211> LENGTH: 41
<212> TYPE: DNA
<213> ORGANISM: Artificial Sequence
<220> FEATURE:
<223> OTHER INFORMATION: antiCR1
<220> FEATURE:
<221> NAME/KEY: modified_base
<222> LOCATION: (1)..(2)
<223> OTHER INFORMATION: Phosphorothioate linkages
<220> FEATURE:
<221> NAME/KEY: misc_feature
<222> LOCATION: (1)..(26)
<223> OTHER INFORMATION: DNA
<220> FEATURE:
<221> NAME/KEY: misc_feature
<222> LOCATION: (27)..(41)
<223> OTHER INFORMATION: RNA
<220> FEATURE:
<221> NAME/KEY: modified_base
<222> LOCATION: (27)..(41)
<223> OTHER INFORMATION: 2-Prime-fluoro nucleotides

<400> SEQUENCE: 17
ccgtggtatt ggaaacaata ccacggauuu uaacuugcua u                            41

<210> SEQ ID NO 18
<211> LENGTH: 41
<212> TYPE: DNA
<213> ORGANISM: Artificial Sequence
<220> FEATURE:
<223> OTHER INFORMATION: antiCR2
<220> FEATURE:
<221> NAME/KEY: modified_base
<222> LOCATION: (1)..(2)
<223> OTHER INFORMATION: Phosphorothioate linkages
<220> FEATURE:
<221> NAME/KEY: misc_feature
<222> LOCATION: (1)..(26)
<223> OTHER INFORMATION: DNA
<220> FEATURE:
<221> NAME/KEY: modified_base
<222> LOCATION: (27)..(29)
<223> OTHER INFORMATION: 2-Prime-fluoro nucleotides
<220> FEATURE:
<221> NAME/KEY: misc_feature
<222> LOCATION: (27)..(41)
<223> OTHER INFORMATION: RNA
<220> FEATURE:
<221> NAME/KEY: modified_base
<222> LOCATION: (30)..(30)
<223> OTHER INFORMATION: Locked nucleic acid
```

-continued

```
<220> FEATURE:
<221> NAME/KEY: modified_base
<222> LOCATION: (31)..(32)
<223> OTHER INFORMATION: 2-Prime-fluoro nucleotides
<220> FEATURE:
<221> NAME/KEY: modified_base
<222> LOCATION: (33)..(33)
<223> OTHER INFORMATION: Locked nucleic acid
<220> FEATURE:
<221> NAME/KEY: modified_base
<222> LOCATION: (34)..(35)
<223> OTHER INFORMATION: 2-Prime-fluoro nucleotides
<220> FEATURE:
<221> NAME/KEY: modified_base
<222> LOCATION: (36)..(36)
<223> OTHER INFORMATION: Locked nucleic acid
<220> FEATURE:
<221> NAME/KEY: modified_base
<222> LOCATION: (37)..(41)
<223> OTHER INFORMATION: 2-Prime-fluoro nucleotides

<400> SEQUENCE: 18
ccgtggtatt ggaaacaata ccacggauut uaacutgcua u                          41

<210> SEQ ID NO 19
<211> LENGTH: 42
<212> TYPE: RNA
<213> ORGANISM: Artificial Sequence
<220> FEATURE:
<223> OTHER INFORMATION: Polynucleotide
<220> FEATURE:
<221> NAME/KEY: misc_feature
<222> LOCATION: (1)..(20)
<223> OTHER INFORMATION: n is a, c, g, or u

<400> SEQUENCE: 19
nnnnnnnnnn nnnnnnnnnn guuuuagagc uaugcuguuu ug                         42

<210> SEQ ID NO 20
<211> LENGTH: 69
<212> TYPE: RNA
<213> ORGANISM: Artificial Sequence
<220> FEATURE:
<223> OTHER INFORMATION: Polynucleotide

<400> SEQUENCE: 20
aaacagcaua gcaaguuaaa auaaggcuag uccguuauca acuugaaaaa guggcaccga      60
gucggugcu                                                             69

<210> SEQ ID NO 21
<211> LENGTH: 42
<212> TYPE: RNA
<213> ORGANISM: Artificial Sequence
<220> FEATURE:
<223> OTHER INFORMATION: Polynucleotide

<400> SEQUENCE: 21
gggcgaggag cguucaccg guuuuagagc uaugcuguuu ug                          42

<210> SEQ ID NO 22
<211> LENGTH: 69
<212> TYPE: RNA
<213> ORGANISM: Artificial Sequence
<220> FEATURE:
<223> OTHER INFORMATION: Polynucleotide

<400> SEQUENCE: 22
aaacagcaua gcaaguuaaa auaaggcuag uccguuauca acuugaaaaa guggcaccga      60
```

-continued

```
gucggugcu                                                                    69

<210> SEQ ID NO 23
<211> LENGTH: 18
<212> TYPE: RNA
<213> ORGANISM: Artificial Sequence
<220> FEATURE:
<223> OTHER INFORMATION: Polynucleotide that Interacts with a Guide
      Sequence of a crRNA or an Equivalent Position of a Single-Guide
      RNA
<220> FEATURE:
<221> NAME/KEY: modified_base
<222> LOCATION: (1)..(18)
<223> OTHER INFORMATION: 2-Prime-O-methyl ribonucleotides
<220> FEATURE:
<221> NAME/KEY: modified_base
<222> LOCATION: (3)..(5)
<223> OTHER INFORMATION: Phosphorothioate linkages

<400> SEQUENCE: 23
cggugaacag cuccucgc                                                          18

<210> SEQ ID NO 24
<211> LENGTH: 17
<212> TYPE: RNA
<213> ORGANISM: Artificial Sequence
<220> FEATURE:
<223> OTHER INFORMATION: Anti1_tracr
<220> FEATURE:
<221> NAME/KEY: modified_base
<222> LOCATION: (1)..(17)
<223> OTHER INFORMATION: 2-Prime-O-methyl ribonucleotides

<400> SEQUENCE: 24
uuauuuuaac uugcuau                                                           17
```

ANTI-CRISPR NUCLEIC ACID INHIBITORS OF CRISPR-CAS EFFECTOR ENZYMES

This application is a U.S. National Phase Application of International Application No. PCT/US2019/053891 filed on Sep. 30, 2019, which claims the benefit of priority from U.S. Provisional Patent Application 62/738,472 filed on Sep. 28, 2018, the disclosures of both of which are incorporated herein by reference.

FIELD OF THE INVENTION

The present disclosure is generally related to molecules for inhibiting CRISPR enzymes.

BACKGROUND OF THE INVENTION

The discovery of gene editing and programmable genomic control by clustered regularly interspaced short palindromic repeat (CRISPR) RNAs (crRNAs) and their CRISPR-associated (CAS) proteins holds tremendous promise for future therapeutics and curing genetic disease. The prototypical CRISPR-associated protein, Cas9 from *S. pyogenes*, naturally binds two RNAs, a CRISPR RNA (crRNA) guide and a trans-acting CRISPR RNA (tracrRNA), to assemble a CRISPR ribonucleoprotein (crRNP). Despite the potential, CRISPR enzymes suffer from several disadvantages in use, such as potential off-target effects that can be exacerbated when uncontrolled. The safety of CRISPR, such as unforeseen adverse events in patients, remains an important concern for practical drug development. To fully implement safe CRISPR-based therapeutics, it may be necessary to develop "kill switch" inhibitors that can halt activity of CRISPR. Several therapeutic drugs have required development of fail-safe antidotes to counter unexpected side effects and protect patients. For example, vitamin K and prothrombin complex concentrations are used as antidotes to reverse adverse reactions or overdoses of anticoagulants like warfarin.

Natural anti-CRISPR proteins have been found in bacteria and bacteriophage genomes that can shut down CRISPR systems by inhibiting DNA binding or blocking conformational state changes required for catalysis. Recent characterization of natural anti-CRISPR proteins, such as AcrIIA2/4, provides inspiration for design of biomolecules that may serve as drugs to mitigate potential problems with CRISPR-based therapies.

There is an urgent need to develop strategies and molecules that can inhibit CRISPR either for safety concerns or to optimize specificity of enzymes. Other than the recent (2017) findings of natural anti-CRISPR proteins, which have not been developed therapeutically, there are currently no technologies for effectively inhibiting CRISPR enzymes or CRISPR-based mechanisms with drug-like molecules. The nucleic acid-based inhibitors described here are substantially smaller than the known anti-CRISPR proteins and can be further engineered with additional chemical modifications, which allows for tuning drug-like properties and making them much better drug candidates than anti-CRISPR proteins. Several nucleic acid-based drugs are now FDA approved and nucleic acids are emerging as an exciting new class of drugs. Currently, therapeutic nucleic acid molecules can be used for target organs and tissues, like the liver, brain and central nervous system. Tissues amenable to delivery of these agents are expected to grow. In addition, the CRISPR inhibitors described here have useful applications in basic research and biotechnology.

SUMMARY OF THE INVENTION

In a general and overall sense, the invention provides a variety of inhibitor molecules having an ability to inhibit a CRISPR enzyme. In some embodiments, these inhibitor molecules comprise an artificial nucleic acid construct.

In some aspects, the inhibitor molecule may comprise an artificial nucleic acid construct having a first polynucleotide. This first polynucleotide may be selected from the group consisting of: a polynucleotide that interacts with a protospacer adjacent motif (PAM)-interaction (PI) domain of a CRISPR-associated (Cas) protein, a polynucleotide that interacts with a guide sequence of a crRNA or an equivalent position of a single-guide RNA, and a polynucleotide that interacts with a repeat region of a tracrRNA or an equivalent position of a single-guide RNA. In a particular embodiment, the first polynucleotide may be a polynucleotide that interacts with a PI domain of a Cas protein In another aspect, the inhibitor molecule may comprise a first polynucleotide, a second polynucleotide and a linker. By way of example, the first polynucleotide may be a polynucleotide that interacts with a PI domain of a Cas protein. In some embodiments, the second polynucleotide may be selected from the group consisting of a polynucleotide that interacts with a guide sequence of a crRNA or an equivalent position of a single-guide RNA, and a polynucleotide that interacts with a repeat region of a tracrRNA or an equivalent position of a single-guide RNA. Preferably, the linker molecule may be operably connected to the first polynucleotide and operably connected to the second polynucleotide.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein. However, those of skill in the art will understand that the drawings, described below, are for illustrative purposes only. The drawings are not intended to limit the scope of the present teachings in any way.

FIG. 1A-FIG. 1B. FIG. 1A contains information regarding nucleic acid constructs employed in the present invention, identified as SEQ ID NO: 2, 3, 7, 8, 9, 10, 11, 12, 13, 14, 15, 16, 17 and 18 (See Table 1).

| | | |
|---|---|---|
| SEQ ID NO: 2 -Anti1_PAM | DNA | Artificial Sequence |
| SEQ ID NO: 3 -Anti1_tracr | RNA | Artificial Sequence |
| SEQ ID NO: 7 -Anti1_crEGIP | RNA | Artificial Sequence |
| SEQ ID NO: 8 -Anti1_PAM-crEGIP | DNA-RNA | Artificial Sequence |
| SEQ ID NO: 9 -Anti_PAM-tracr | DNA-2'-O—CH$_3$RNA | Artificial Sequence |
| SEQ ID NO: 11 -Anti1_PAM-tracr | DNA-2'-O—CH$_3$RNA | Artificial Sequence |
| SEQ ID NO: 10 - Anti2-PAM-tracr_RNA | DNA-RNA | Artificial Sequence |
| SEQ ID NO: 12 - antiCR1 | DNA-FRNA | Artificial Sequence |
| SEQ ID NO: 13 - antiCR2 | DNA-FRNA-LNA | Artificial Sequence |
| SEQ ID NO: 14 -Anti1_PAM-tracer | DNA-2'-O—CH3RNA | Artificial Sequence |

3

-continued

| SEQ ID NO: 15 -Anti2__PAM-tracer | DNA-2'-O—CH3RNA | Artificial Sequence |
| SEQ ID NO: 16 -Anti2__PAM-tracer_RNA | DNA-2'-O—CH3RNA | Artificial Sequence |
| SEQ ID NO: 17 - antiCR1 | DNA-FRNA | Artificial Sequence |
| SEQ ID NO: 18 - antiCR2 | DNA-FRNA-LNA | Artificial Sequence |

Figure 1B:
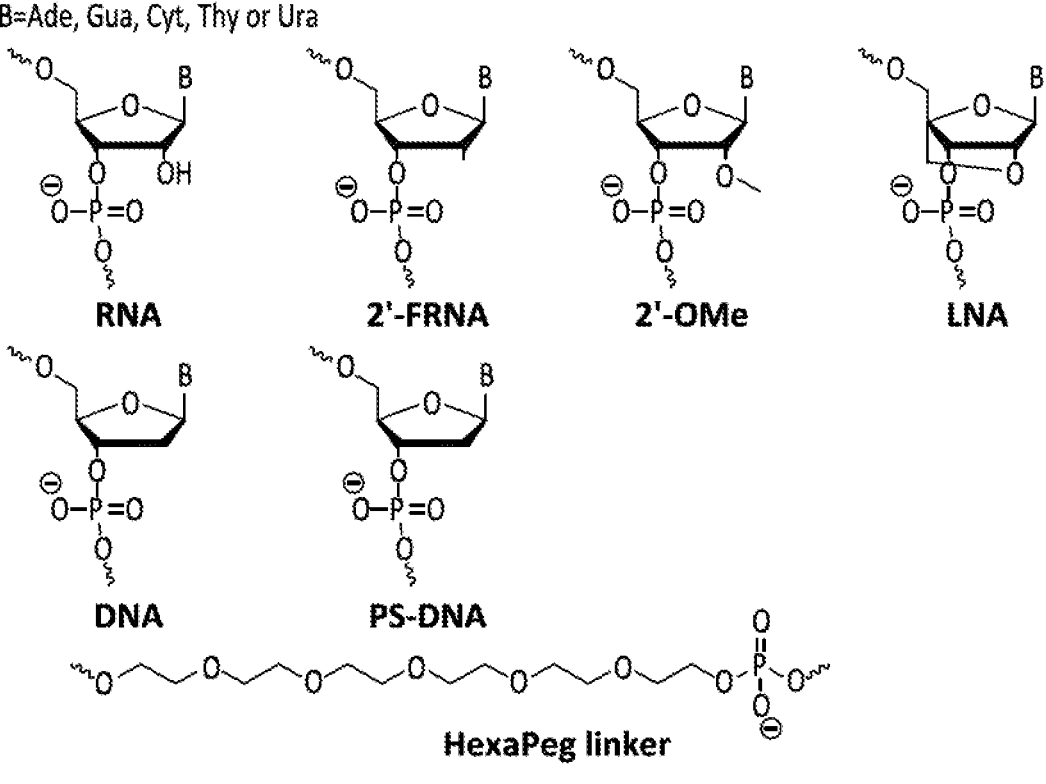

FIG. 1B is a series of chemical drawings illustrating the chemical modifications used in the Examples.

Figure 2:
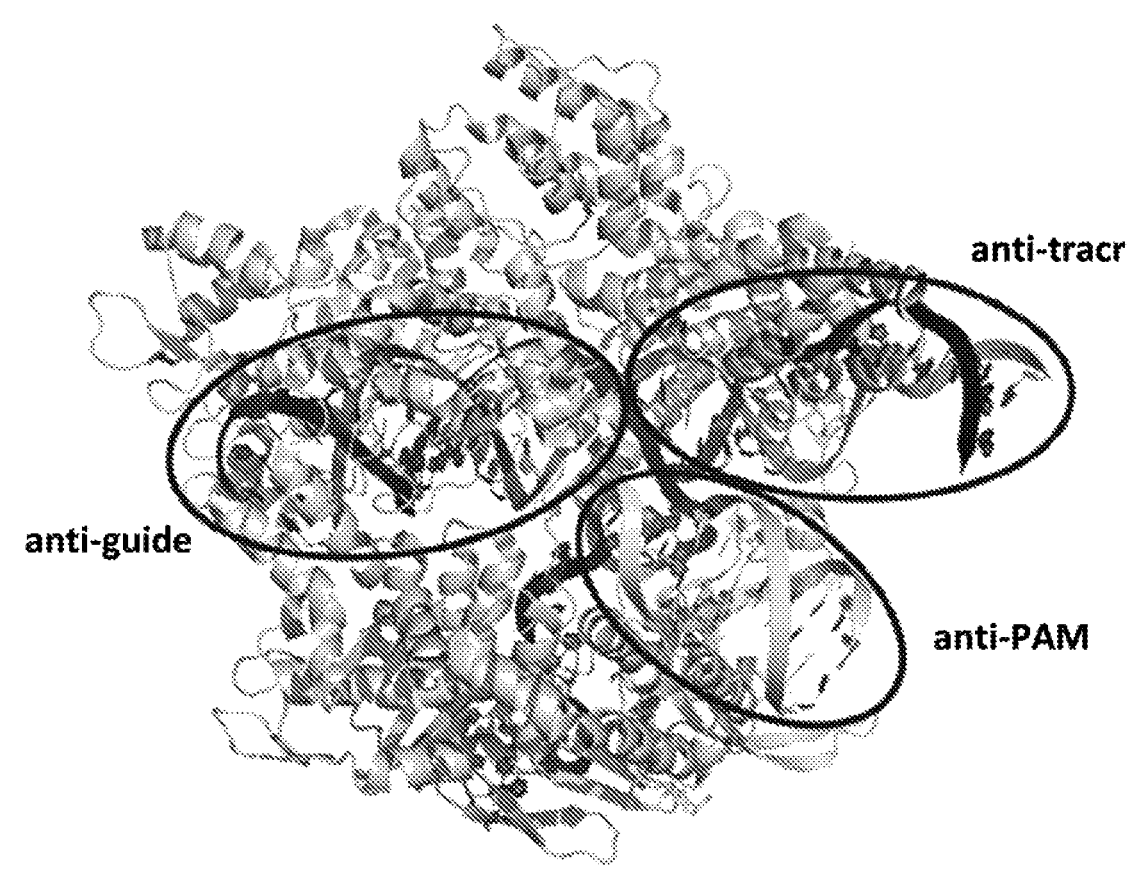

FIG. 2 is a drawing showing possible points of contact for nucleic acid-based inhibitors to CRISPR-Cas enzymes. Anti-guide modules will base-pair with the crRNA or sgRNA guide sequence, anti-tracr modules will base-pair with the tracrRNA repeat region, and anti-PAM modules will interact with the CAS protein PAM-interaction (PI) domain.

Figures 3A, 3B, 3C, 3D, 3E:
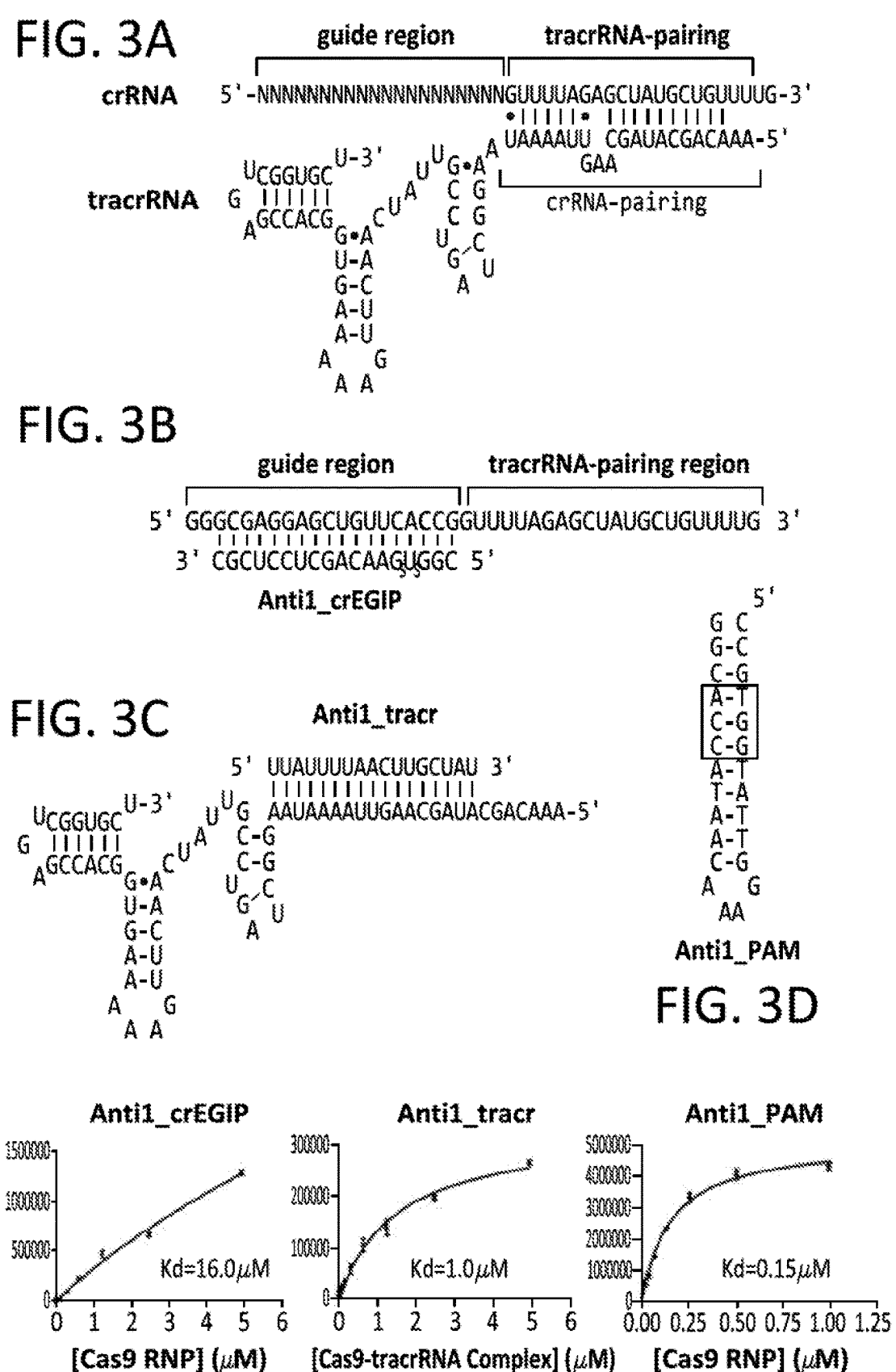

FIG. 3A-FIG. 3E. Presented is a series of drawings and graphs illustrating single contact point inhibitors and their binding affinity for Cas9 RNP. (3A) FIG. 3A depicts a crRNA than can comprise the sequence of SEQ. ID. NO. 19 in contact with a tracrRNA that can comprise the sequence of SEQ. ID. NO. 20. Illustration of a dual RNA guide system (crRNA+tracrRNA). (3B-3D) FIGS. 3B-3D depict the sequences and structure of single contact point inhibitors against the crRNA guide comprising SEQ. ID. NO. 21 or SEQ. ID. NO. 22 (Anti1-crEGIP SEQ. ID. NO. 7 or SEQ. ID. NO. 24), the tracrRNA repeat (Anti1-tracr SEQ. ID. NO 3 or SEQ. ID. NO. 23), and the PI domain of Cas9 (Anti1-PAM SEQ. ID. NO. 2). (3E) Binding isotherms and calculated affinity of single contact point inhibitors for the Cas9-tracrRNA RNP complex determined by dot-blot. Error bars are standard error of the mean (s.e.m.).

FIG. 4A-FIG. 4E. Presented is a series of drawings and graphs illustrating multiple contact point inhibitors and their binding affinity for Cas9 RNP. (4A-4D) FIGS. 4A-4D depict the sequences and structure of single contact point inhibitors against the crRNA guide comprising SEQ. ID. NO. 21 or SEQ. ID. NO. 22 wherein the inhibitors can comprise at least one of sequences Anti1_PAMcrEGIP (SEQ. ID. NO. 8), Anti1_PAM-tracr (SEQ. ID. NO. 9 or SEQ. ID. NO. 14), and Anti2_PAM-tracr_RNA (SEQ. ID. NO. 10 or SEQ. ID. NO. 16). Sequence and structure of multiple contact point inhibitors. (4E) Binding isotherms and calculated affinity of multiple contact point inhibitors for the Cas9-tracrRNA RNP complex determined by dot-blot. Error bars are standard error of the mean (s.e.m.).

Figure 5A:
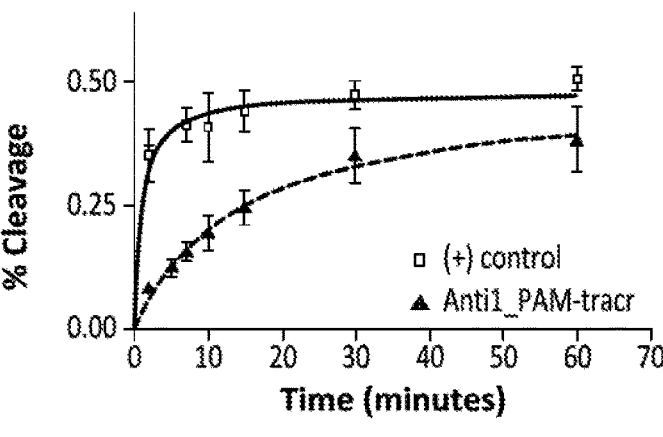
Figure 5B:
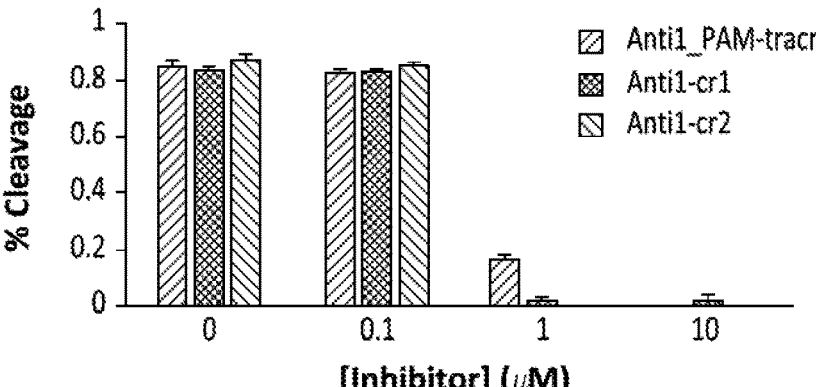
Figure 5C:
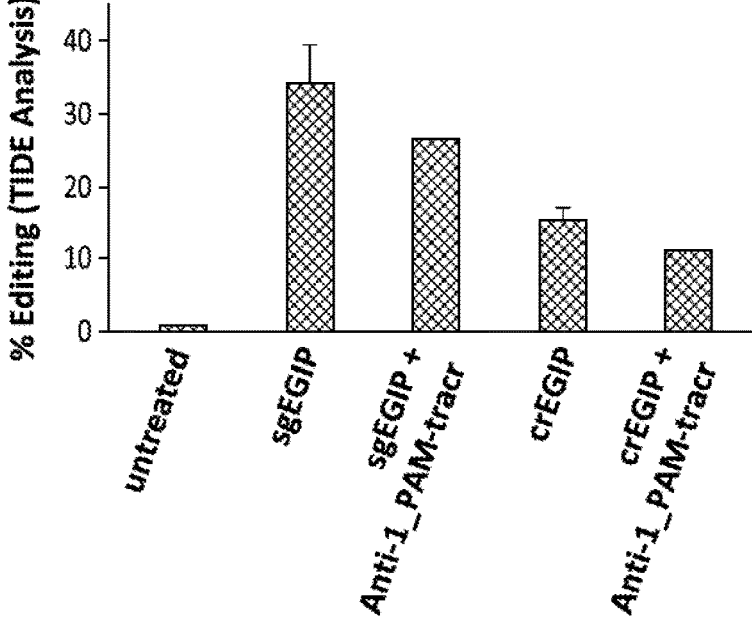

FIG. 5A-FIG. 5C. FIG. 5A is a series of graphs depicting inhibition of Cas9 catalytic activity by model inhibitor prototypes. (5A) Inhibition of Cas9 activity over time by the Anti1_PAM-tracr inhibitor set at 10 µM. (5B) Inhibition of a 10 min cleavage assay reaction with varying concentrations of Anti1_PAM-tracr (SEQ ID NO: 9), Anti1-cr1 (SEQ ID NO: 12) and Anti1-cr2 inhibitors (SEQ ID NO: 13). (5C) Inhibition of cell-based editing by Anti1_PAM-tracr. Error bars are standard error of the mean (s.e.m.).

Figure 6A:
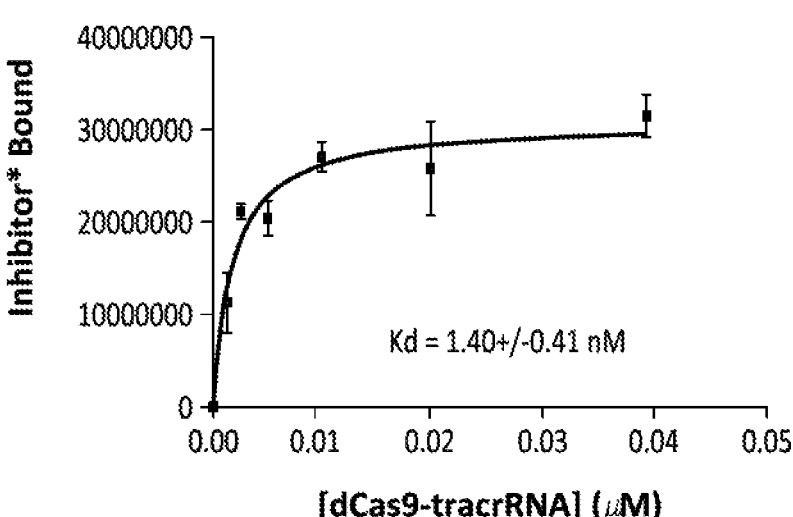
Figure 6B:
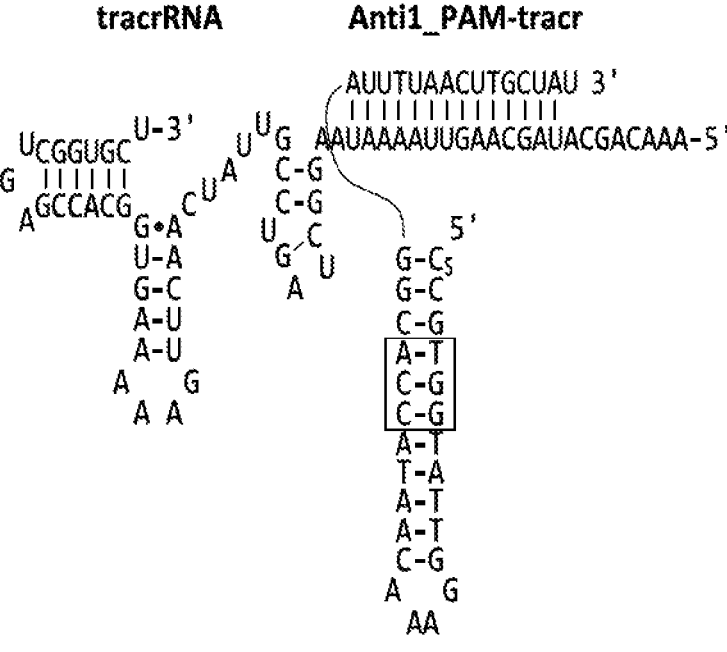

FIG. 6A FIG. 6B. A binding curve and a calculated affinity as determined by dot blot (FIG. 6A) of a chemically modified Anti1_PAM-tracer (SEQ. ID. NO. 9 or SEQ. ID. NO. 14) inhibitor design (FIG. 6B). Error bars are standard error of the mean (SEM).

Figure 7:
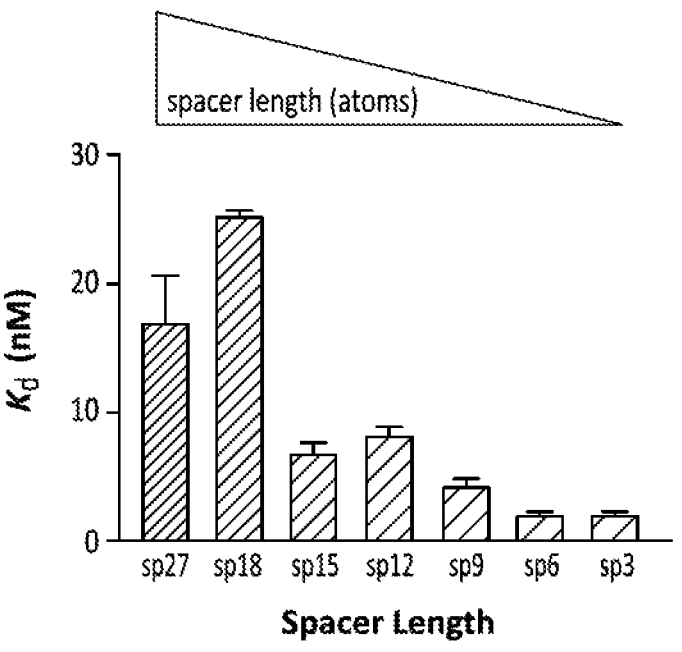

FIG. 7 presents binding curves and calculated affinities of spacer length variants. Binding affinity was determined by dot blot filter assay. Error bars are standard error of the mean (SEM).

4

Figure 8:
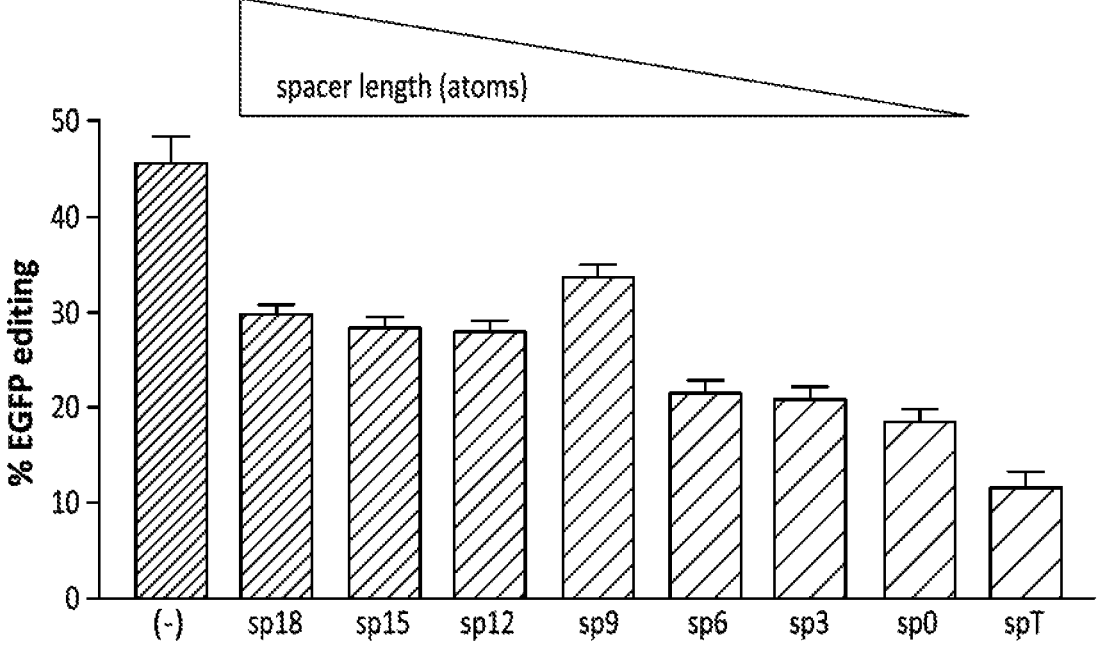

FIG. 8 presents inhibition of CRISPR-Cas9 Editing in human cells by spacer length inhibitor variants. Inhibitors were lipid co-transfected with a single guide RNA targeting EGFP into Cas9 and EGFP expressing HEK293T cells. Editing was measured as loss of EGFP signal in flow cytometry analysis. Error bars are standard error of the mean (SEM). EGFP, enhanced green fluorescent protein.

DETAILED DESCRIPTION OF THE INVENTION

The present disclosure provides CRISPR inhibitor molecules comprising an artificial nucleic acid construct. In some aspects, the artificial nucleic acid construct comprises a first polynucleotide selected from the group consisting of: a polynucleotide that interacts with a protospacer adjacent motif (PAM)-interaction (PI) domain of a CRISPR-associated (Cas) protein, a polynucleotide that interacts with a guide sequence of a crRNA or an equivalent position of a single-guide RNA, and a polynucleotide that interacts with a repeat region of a tracrRNA or an equivalent position of a single-guide RNA.

In some embodiments, the first polynucleotide may be a polynucleotide that interacts with a PI domain of a Cas protein.

In another embodiment, the first polynucleotide may be a polynucleotide that interacts with a guide sequence of a crRNA or an equivalent position of a single-guide RNA.

In yet another embodiment, the first polynucleotide may be a polynucleotide that interacts with a repeat region of a tracrRNA or an equivalent position of a single-guide RNA.

In another aspect, the CRISPR inhibitor molecule comprises a nucleic acid construct having a first polynucleotide selected from the group consisting of: a polynucleotide that interacts with a protospacer adjacent motif (PAM)-interaction (PI) domain of a CRISPR-associated (Cas) protein, a polynucleotide that interacts with a guide sequence of a crRNA or an equivalent position of a single-guide RNA, and a polynucleotide that interacts with a repeat region of a tracrRNA or an equivalent position of a single-guide RNA, a second polynucleotide and a linker molecule. In a particular embodiment, the first polynucleotide may be a polynucleotide that interacts with a PI domain of a Cas protein.

The polynucleotide component of the polynucleotide constructs described herein that interacts with a protospacer adjacent motif (PAM), may further be described as an anti-PAM oligonucleotide. The anti-PAM oligonucleotide may comprise a stem-loop (hairpin) polynucleotide construct. The loops, by way of example, may comprise DNA, RNA, ANA, FANA, 2'5'-linked RNA, or any combination thereof. FANA and ANA refer to 2'-deoxy-2'-fluoroarabino-nucleic acid and arabinonucleic acid, respectively. The stem in the polynucleotide hairpin may comprise DNA or DNA analogs such as FANA, ANA, or any combination of these.

The second polynucleotide may be selected from the group consisting of a polynucleotide that interacts with a guide sequence of a crRNA or an equivalent position of a single-guide RNA, and a polynucleotide that interacts with a repeat region of a tracrRNA or an equivalent position of a single-guide RNA. Preferably, the linker molecule may be operably connected to the first polynucleotide and operably connected to the second polynucleotide. In some embodiments, the first polynucleotide may be a polynucleotide that interacts with a PI domain of a Cas protein.

The CRISPR inhibitor molecule may comprise an artificial nucleic acid construct comprising a first polynucleotide, a second polynucleotide and a linker molecule, where the second polynucleotide may be a polynucleotide that inter-acts with a guide sequence of a crRNA or an equivalent position of a single-guide RNA. In some embodiments, the linker molecule may be operably connected to the first polynucleotide and operably connected to the second poly-nucleotide. In those embodiments of the nucleic acid con-struct that are absent a linker, the first polynucleotide and the second polynucleotide may be directly fused to one another.

In some embodiments, the first polynucleotide may be a polynucleotide that interacts with a PI domain of a Cas protein, and the CRISPR inhibitor molecule may further comprise a second polynucleotide and a linker molecule. The second polynucleotide may be a polynucleotide that interacts with a repeat region of a tracrRNA or an equivalent position of a single-guide RNA. Preferably, the linker mol-ecule may be operably connected to the first polynucleotide and operably connected to the second polynucleotide.

In some embodiments, the first polynucleotide that inter-acts with the PI domain of the Cas protein may comprise: 2'-deoxyribonucleotides only, at least one 2'-deoxyribo-nucleic analogs, a mixture of 2'-deoxyribonucleotide and 2'-deoxynucleotide analogs, or 2'-deoxyribonucleotide ana-logs only such as FANA, ANA, alpha-L locked nucleic acid (alpha-L-LNA), phosphorothioate deoxyribonucleic acid (PS-DNA), and combinations of these. Alternatively, the first polynucleotide that interacts with the PI domain of the Cas protein may comprise a sequence of SEQ ID NO: 1 or a sequence at least 95% identical thereto or a functional fragment thereof, or a sequence of SEQ ID NO: 2 or a sequence at least 95% identical thereto or a functional fragment thereof.

In some embodiments, the first polynucleotide that inter-acts with the PI domain of the Cas protein may comprise one or more of the following: 2'-deoxyribonucleotide, a 2'-de-oxyribonucleotide analog, a ribonucleotide, a ribonucleotide analog, or any combination thereof.

In some embodiments, the second polynucleotide that interacts with the guide sequence of the crRNA or the equivalent position of the single-guide RNA may comprise: ribonucleotides only, at least one ribonucleotide analog, a mixture of ribonucleotides and ribonucleotide analogs, or ribonucleotide analogs only such as 2'-FNA, LNA, 2'-OMe RNA, and combinations of these. Alternatively, the second polynucleotide that interacts with the guide sequence of the crRNA or the equivalent position of the single-guide RNA may comprise a sequence of SEQ ID NO: 3 or a sequence at least 95% identical thereto or a functional fragment thereof.

In some embodiments, the second polynucleotide that interacts with the guide sequence of the crRNA or the equivalent position of the single-guide RNA may comprise one or more of the following: a 2'-deoxyribonucleotide, a 2'-deoxyribonucleotide analog, a ribonucleotide, a ribo-nucleotide analog, or any combination thereof.

In further embodiments, the second polynucleotide that interacts with the repeat region of the tracrRNA or the equivalent position of the single-guide RNA may comprise: ribonucleotides only, at least one ribonucleotide analog, a mixture of ribonucleotides and ribonucleotide analogs, or ribonucleotide analogs only. Alternatively, the second poly-nucleotide that interacts with the repeat region of the tracrRNA or the equivalent position of the single-guide RNA may comprise a sequence of: SEQ ID NO: 4 or a sequence at least 95% identical thereto or a functional fragment thereof, SEQ ID NO: 5 or a sequence at least 95% identical thereto or a functional fragment thereof, SEQ ID NO: 6 or a sequence at least 95% identical thereto or a functional fragment thereof, or SEQ ID NO: 7 or a sequence at least 95% identical thereto or a functional fragment thereof.

In further embodiments, the second polynucleotide that interacts with the repeat region of the tracrRNA or the equivalent position of the single-guide RNA may comprise one or more of the following: a 2'-deoxyribonucleotide, a 2'-deoxyribonucleotide analog, a ribonucleotide, a ribo-nucleotide analog, or any combination thereof.

In another embodiment, the linker molecule may com-prise polyethylene glycol. Alternatively, the linker molecule may comprise poly-deoxythymidylic acid (poly-dT), or any other single stranded oligonucleotide with spacer function-ality. The linker molecule may generally comprise a poly-nucleic acid of any chemistry. The linker may also generally comprise a single nucleic acid of any chemistry.

In another embodiment, the CRISPR inhibitor molecule comprises a nucleic acid construct having a first polynucle-otide and a second polynucleotide. The first polynucleotide may be operably connected to the second polynucleotide. In some embodiments, the first polynucleotide and the second polynucleotide may be directly fused to one another.

In yet another embodiment, the Cas protein may comprise Cas9, Cas12a (Cpf1), or dead Cas9 (dCas9). Alternatively, the Cas protein may be any other suitable CAS protein from a CRISPR system. The CRISPR system may be natural or synthetic. In some embodiments, the Cas protein is Cas9. While one source of Cas9 protein is from *Streptococcus pyogenes*, other sources of Cas protein known to those of skill in the art may also be used. Other sources of Cas protein include, but are not limited to, *Staphylococcus aureus, Campylobacter jejuni, Neisseria meningitides, Francisilla Novicida, Streptococcus* thermophiles, *Geobacillus stearo-thermophilus*, and numerous other bacterial species.

2'-deoxyribonucleotides of the present invention are gen-erally understood to refer to 2'-deoxyribonucleic acid mol-ecules that do not contain any chemical modifications.

2'-deoxyribonucleotide analogs of the present invention include any suitable chemically modified nucleotide that maintains the properties of a 2'-deoxyribonucleotide, or mimics a 2'-deoxyribonucleotide in certain properties, including base pairing and Cas9 interaction. A number of 2'-deoxyribonucleotide analogs are well-known to a person of skill in the art and can be used in certain embodiments of the present invention. Examples include, but are not limited to, arabinonucleic acid (ANA), 2'-fluoro-arabinonucleic acid (FANA), alpha-L locked nucleic acid (alpha-L-LNA), phos-phorothioate deoxyribonucleic acid (PS-DNA), acyclic or unlocked nucleic acid (UNA), or any combination thereof.

Ribonucleotides of the present invention are generally understood to refer to ribonucleic acid molecules that do not contain any chemical modifications.

Ribonucleotide analogs of the present invention include any suitable chemically modified nucleotide that maintains the properties of a ribonucleotide, or mimics a ribonucle-otide with respect to certain properties, including base pairing or Cas9 interaction. A number of ribonucleotide analogs are well-known to a person of skill in the art and can be used in certain embodiments of the present invention. Examples include, but are not limited to, 2'-fluorinated ribonucleic acid (2'-FRNA), 2',5'-linked ribonucleic acid (2',5'-RNA), 2'-O-methyl ribonucleic acid (2'-OMe-RNA), 2'-methoxyethyl ribonucleic acid (2'-MOE-RNA), 2'-fluori-nated-4'-O-methyl ribonucleic acid (2'F,4'OMe-RNA), 2',4'-di-O-methyl ribonucleic acid (2',4'-diOMe-RNA), 2',4' difluorinated ribonucleic acid (2',4'-di-RNA), locked nucleic acid (LNA), and bicyclic or bridged nucleic acid (BNA), or any combination thereof.

While most of the polynucleotides disclosed herein have conventional phosphodiester internucleotide linkages and are suitable for use in the disclosed embodiments, other internucleotide linkages are well-known to the skilled artisan and can be used in additional embodiments of the present disclosure. Thus the present disclosure also provides polynucleotides that have one or more internucleotide linkages that are not a phosphodiester internucleotide linkage. In some embodiments, the polynucleotides comprises at least one internucleotide linkage selected from the group consisting of phosphodiester, phosphorothioate, phosphotriester, phosphorodithioate, boranophosphate, Rp- and/or Sp-phosphorothioate, 3' thioformacetal, methylene, amide, methylphosphonate, phosphoramidate, amide and any combination thereof.

Expression vectors including the artificial nucleic acid constructs of the present disclosure are also provided. These expression vectors may comprise a plasmid or virus. The nucleic acid constructs of the present disclosure may contain a promoter operably linked to a transcribable nucleic acid molecule operably linked to a 3' transcription termination nucleic acid molecule. In addition, the artificial nucleic acid constructs may further include, but are not limited to, additional regulatory nucleic acid molecules from, e.g., the 3'-untranslated region (3' UTR). The nucleic acid constructs can also include a 5' untranslated region (5' UTR) of an mRNA nucleic acid molecule. This 5' UTR will serve, by way of example, a role in translation initiation and provide a genetic component as part of an expression vector. These additional upstream and downstream regulatory nucleic acid molecules and sequences may be derived from a source that is native or heterologous with respect to the other elements present in the artificial nucleic acid constructs described herein.

Definitions

The following definitions and methods are provided to better define the present invention and to guide those of ordinary skill in the art in the practice of the present invention. Unless otherwise noted, terms are to be understood according to conventional usage by those of ordinary skill in the relevant art. Unless defined otherwise, all technical and scientific terms used herein have the same meaning as commonly understood by one of skill in the art to which the disclosure pertains. Although any methods and materials similar to or equivalent to those described herein can be used in the practice or testing of the present technology, the preferred methods and materials are described herein.

Reference to an element by the indefinite article "a" or "an" does not exclude the possibility that more than one element is present, unless the context clearly requires that there be one and only one element. The indefinite article "a" or "an" thus usually means "at least one."

As used herein, "patient" or "subject" means an individual having symptoms of, or at risk for, cancer, disease or other malignancy. A patient may be human or non-human and may include, for example, an animal such as a horse, dog, cow, pig or other animal. Likewise, a patient or subject may include a human patient including adults or juveniles (e.g., children). Moreover, a patient or subject may mean any living organism, preferably a mammal (e.g., human or non-human) from whom a blood volume is desired to be determined and/or monitored from the administration of compositions contemplated herein.

As used herein, "about" means within a statistically meaningful range of a value or values such as a stated concentration, length, molecular weight, pH, sequence identity, timeframe, temperature or volume. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art. As used herein, the terms "subject" and "patient" are used interchangeably irrespective of whether the subject has or is currently undergoing any form of treatment.

As used herein, the terms "subject" and "subjects" refer to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgus monkey, chimpanzee, etc.) and a human). Preferably, the subject is a human.

The term "construct" is understood to refer to any recombinant or synthetic polynucleotide molecule such as a plasmid, cosmid, virus, autonomously replicating polynucleotide molecule, phage, or linear or circular single-stranded or double-stranded DNA or RNA polynucleotide molecule, derived from any source, biological or chemical, capable of genomic integration or autonomous replication, comprising a polynucleotide molecule where one or more polynucleotide molecule has been linked in a functionally operative manner, i.e. operably linked.

An "expression vector", "vector", "vector construct", "expression construct", "plasmid", or "recombinant DNA construct" is generally understood to refer to a nucleic acid that has been generated via human intervention, including by recombinant means or direct chemical synthesis, with a series of specified nucleic acid elements that permit transcription or translation of a particular nucleic acid in, for example, a host cell. The expression vector can be part of a plasmid, virus, or nucleic acid fragment. Typically, the expression vector can include a nucleic acid to be transcribed operably linked to a promoter.

The terms "heterologous DNA sequence", "exogenous DNA segment" or "heterologous nucleic acid," as used herein, each refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides. Conversely, a homologous DNA sequence is a DNA sequence that is naturally associated with a host cell into which it is introduced.

"Operably linked" or "functionally linked" refers preferably to the association of nucleic acid sequences on a single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation. The two nucleic acid molecules may be part of a single contiguous nucleic acid molecule and may be adjacent. For example, a promoter is operably linked to a gene of interest if the promoter regulates or mediates transcription of the gene of interest in a cell. Operably linked or functionally linked may also refer to the physical connection or nucleic acid sequences.

A "promoter" is generally understood as a nucleic acid control sequence that directs transcription of a nucleic acid. An inducible promoter is generally understood as a promoter that mediates transcription of an operably linked gene in response to a particular stimulus. A promoter can include necessary nucleic acid sequences near the start site of transcription, such as, in the Case of a polymerase II type promoter, a TATA element. A promoter can optionally include distal enhancer or repressor elements, which can be located as much as several thousand base pairs from the start site of transcription.

A "transcribable nucleic acid molecule" as used herein refers to any nucleic acid molecule capable of being transcribed into a RNA molecule. Methods are known for introducing constructs into a cell in such a manner that the transcribable nucleic acid molecule is transcribed into a functional mRNA molecule that is translated and therefore expressed as a protein product. Constructs may also be constructed to be capable of expressing antisense RNA molecules, in order to inhibit translation of a specific RNA molecule of interest. For the practice of the present disclosure, conventional compositions and methods for preparing and using constructs and host cells are well known to one skilled in the art (see e.g.: Ausubel et al.; Elhai and Wolk; Sambrook and Russel, 2001; and Sambrook and Russel, 2006).

Nucleotide and/or amino acid sequence identity percent (%) is understood as the percentage of nucleotide or amino acid residues that are identical with nucleotide or amino acid residues in a candidate sequence in comparison to a reference sequence when the two sequences are aligned. To determine percent identity, sequences are aligned and if necessary, gaps are introduced to achieve the maximum percent sequence identity. Sequence alignment procedures to determine percent identity are well known to those of skill in the art. Often publicly available computer software such as BLAST, BLAST2, ALIGN2 or Megalign (DNASTAR) software is used to align sequences. Those skilled in the art can determine appropriate parameters for measuring alignment, including any algorithms needed to achieve maximal alignment over the full-length of the sequences being compared. When sequences are aligned, the percent sequence identity of a given sequence A to, with, or against a given sequence B (which can alternatively be phrased as a given sequence A that has or comprises a certain percent sequence identity to, with, or against a given sequence B) can be calculated as: percent sequence identity=X/Y100, where X is the number of residues scored as identical matches by the sequence alignment program's or algorithm's alignment of A and B and Y is the total number of residues in B. If the length of sequence A is not equal to the length of sequence B, the percent sequence identity of A to B will not equal the percent sequence identity of B to A.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

The ten is "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present disclosure.

Having described the present disclosure in detail, it will be apparent that all of the compositions and methods disclosed and claimed herein can be made and executed without undue experimentation in light of the present disclosure. While the compositions and methods of this disclosure have been described in tennis of preferred embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. Furthermore, it should be appreciated that all examples in the present disclosure are provided as non-limiting examples.

The following Table 1 provides a series of nucleic acid constructs.

TABLE 1

| Name | Mods | Sequences (5'-3') | Mass calculated | Mass found | Length |
|---|---|---|---|---|---|
| Anti1_crEGIP SEQ ID NO: 7 | 2'-O-CH₃ RNA | CGGₛUₛGAACAGCUCCUCGC | 5991.10 | 5991.50 | 18 |
| Anti1_tracr SEQ ID NO: 3 | 2'-O-CH₃ RNA | UUA UUU UAA CUU GCU AU | 5510.60 | 5511.20 | 17 |
| Anti1_PAM SEQ ID NO: 2 | DNA | *CCG TGG TAT TGG AAA CAA TAC CAC GG* | 8004.20 | 8005.20 | 26 |
| Anti1_PAM-crEGIP SEQ ID NO: 8 | DNA-2'-O-CH₃RNA | *CₛCG TGG TAT TGG AAA CAA TAC CAC GG*ₛUₛGAA CAG CUC CUC GC | 13065.70 | 13067.60 | 41 |
| Anti1_PAM-tracr SEQ ID NO: 9 | DNA-2'-O-CH₃RNA | *CₛCG TGG TAT TGG AAA CAA TAC CAC GG*-(Hexa PEG)-AUU UUA ACU UGC UAU | 13296.80 | 13297.40 | 44 |
| Anti2_PAM-tracr SEQ ID NO: 11 | DNA-2'-O-CH₃RNA | *CₛCG TGG TAT TGG AAA CAA TAC CAC GG*-(Hexa PEG)-GUU UUA GAG CUAUGC UGU | 14374.40 | 14375.80 | 44 |
| Anti2_PAM-tracr_RNA SEQ ID NO: 10 | DNA-RNA | *CₛCG TGG TAT TGG AAA CAA TAC CAC GG*-(Hexa PEG)-GUU UUA GAG CUAUGC UGU | 14121.90 | 14124.40 | 44 |
| antiCR1 SEQ ID NO: 12 | DNA-FRNA | *CₛCG TGG TAT TGG AAA CAA TAC CAC GG*-(Hexa PEG)-**A\*U\*U\* U\*U\*A\* A\*C\*U\* U\*G\*C\* U\*A\*U\*** | 13116.36 | 13116.27 | 41 |
| antiCR2 SEQ ID NO: 13 | DNA-FRNA-LNA | *CₛCG TGG TAT TGG AAA CAA TAC CAC GG*-(Hexa PEG)-**A\*U\*U\*** *U̲U̲*\*A\* *A̲C̲*\*U\* *U̲G̲*\***C\* U\*A\*U\*** | 13174.42 | 13174.03 | 41 |
| Anti1_PAM-tracr SEQ ID NO: 14 | DNA-2'-O-CH₃RNA | *CₛCG TGG TAT TGG AAA CAA TAC CAC GG*-(Linker)-AUU UUA ACU UGC UAU | 13296.80 | 13297.40 | 44 |
| Anti2_PAM-tracr SEQ ID NO: 15 | DNA-2'-O-CH₃ RNA | *CₛCG TGG TAT TGG AAA CAA TAC CAC GG*-(Linker)-GUU UUA GAG CUAUGC UGU | 14374.40 | 14375.80 | 44 |
| Anti2_PAM-tracr_RNA SEQ ID NO: 16 | DNA-RNA | *CₛCG TGG TAT TGG AAA CAA TAC CAC GG*-(Linker)-GUU UUA GAG CUAUGC UGU | 14121.90 | 14124.40 | 44 |
| antiCR1 SEQ ID NO: 17 | DNA-FRNA | *CₛCG TGG TAT TGG AAA CAA TAC CAC GG*-(Linker)-**A\*U\*U \*U\*U\*A\* A\*C\*U\* U\*G\*C\* U\*A\*U\*** | 13116.36 | 13116.27 | 41 |
| antiCR2 SEQ ID NO: 18 | DNA-FRNA-LNA | *CₛCG TGG TAT TGG AAA CAA TAC CAC GG*-(Linker)-**A\*U\*U\*** *U̲U̲*\*A\* *A̲C̲*\*U\* *U̲G̲*\***C\* U\*A\*U\*** | 13174.42 | 13174.03 | 41 |

Legend:
DNA = Italics
2'-O-CH₃RNA = Bold and Underlined
RNA = Bold, No Italics, No underline
LNA = Italics and underline (A̲ *T̲*)
FRNA* = a nucleotide that is 2'F (Examples, A*, U*, C*, G*)
Linker = a nucleotide linker, examples are 3 atom or 27 atoms polyethylene glycol linkers (an example is Hexa PEG);
ₛ = PS linker

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and this can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1—RNA and Inhibitor Synthesis

Some of the inhibitor molecules and crRNAs were commercially synthesized by Integrated DNA Technologies (IDT), while others were custom synthesized as shown in FIG. 1. The custom synthesized molecules were prepared using standard phosphoramidite solid-phase conditions. Syntheses were performed on an Applied Biosystems 3400 or Expedite DNA Synthesizer at a 1 micromole scale using Unylink CPG support (ChemGenes). All phosphoramidites were prepared as 0.13 M solutions in acetonitrile (ACN), except DNA, which was prepared as 0.1 M solutions. 5-Ethylthiotetrazole (0.25 M in ACN) was used to activate phosphoramidites for coupling. Detritylations were accomplished with 3% trichloroacetic acid in $CH_2Cl_2$ for 110 s. Capping of failure sequences was achieved with acetic anhydride in tetrahydrofuran (THF) and 16% N-methylimidazole in THF. Oxidation was done using 0.1M $I_2$ in 1:2:10 pyridine:water:THF. Coupling times were 30 minutes for 2'F-RNA, and 50 minutes for LNA phosphoramidites. Deprotection and cleavage from the solid support was accomplished with 3:1:0.2 $NH_4OH$:EtOH:DMSO at 65° C. for 16 h. Crude oligonucleotides were purified by anion exchange HPLC on an Agilent 1200 Series Instrument using a Protein-Pak DEAE 5PW column (7.5×75 mm) at a flow rate of 1 mL/min. The gradient was 0-24% solution 1M $LiClO_4$ over 30 mM at 60° C. Samples were desalted on NAP-25 desalting columns according to manufacturer protocol. Modified crRNAs were prepared for RNP assembly by heating to 95° C. then placing on ice to prevent formation of stable secondary structures.

TracrRNA and sgRNA was prepared by T7 in vitro transcription with DNA templates synthesized by IDT. Single-stranded DNA templates were annealed to T7 promoter oligo to generate double-stranded promoter regions, which support in vitro transcription by T7 RNA polymerase. Transcription reactions were performed by standard protocols for 2 hours. Briefly, reactions contained purified T7 RNA polymerase, 30 mM Tris (at pH 7.9), 12.5 mM NaCl, 40 mM MgCl2, 2% PEG8000, 0.05% Triton X-100, 2 mM spermidine, and 2.5 µM T7-DNA template. Afterward, the DNA template was degraded by the addition of 1 unit of DNase I for every 20 µL of reaction and incubated at 37° C. for 15 min. Reactions were phenol-chloroform extracted and gel-purified from denaturing polyacrylamide gels. Purified RNA was quantified by measuring absorbance at 260 nm and calculated extinction coefficients using nearest neighbor approximations and Beer's Law.

Example 2—Preparation of Spy Cas9

Plasmid encoding a Spy Cas9 with a C-terminal fusion of a nuclear localization signal (NLS) and a 6×-Histidine tag (pET-Cas9-NLS-6×His) was obtained from Addgene (62933). A dead Cas9 (dCas9) version was prepared by performing site-directed mutagenesis on this plasmid to generate H840A and D10A mutations (pET-dCas9-NLS-6× His).

Protein expression was induced in Rosetta (DE3) cells with 0.4 mM IPTG at 18° C. for 16 h. Cell pellets were resuspended in 6 mL of chilled binding buffer (20 mM Tris-HCl, pH 8.0, 250 mM NaCl, 1 mM PMSF, 5 mM imidazole) per 0.5 L of culture. Resuspended cells were sonicated and clarified by centrifugation. His-Pur Cobalt-CMA resin (Thermo Scientific) was equilibrated with binding buffer and the supernatant added to the equilibrated resin and incubated at 4° C. for 1 h. The supernatant was washed sequentially with increasing concentrations of NaCl in 50 mL volumes of wash buffer (Tris-HCl, pH 8, 0.25/0.5/0.75/1.0 M NaCl, 10 mM imidazole). Protein was eluted with 15 mL elution buffer (Tris-HCl, pH 8, 250 mM NaCl, 130 mM imidazole). Purified Cas9 was concentrated with Vivaspin 15 centrifugal concentrators (Sartorius, 30K MWCO). Concentration was approximated by UV absorbance at 280 nm using a calculated extinction coefficient (120,450 M−1 cm−1) and Beer's law. One volume of glycerol was added to a final of 50% and purified Cas9 stored as aliquots at −80° C.

Example 3—Radiolabeling of RNA, DNA, and Inhibitors

The 5' phosphate on T7-transcribed tracrRNA was removed using alkaline phosphatase following the manufacturer's recommended protocol. Synthetic duplex target DNA and crRNA lacks a 5' phosphate and was directly labeled. 100 pmols of tracrRNA, crRNA, or antisense DNA target strand was radiolabeled with [γ-32P]-ATP using T4 poly-nucleotide kinase following the manufacturers recommended enzyme protocol. Reactions were phenol-chloroform extracted and radiolabeled RNA or DNA was gel-purified on 15% denaturing polyacrylamide gels (1×TBE, 7 M urea) by the crush-and-soak method. Gel-purified radiolabeled RNA and DNA was quantified by scintillation counting.

Example 4—Determining the Active Concentration of Cas9 and dCas9

The active concentration of Cas9 and dCas9 proteins were determined by titration of increasing amounts of Cas9 or dCas9 with 0.5 µM crRNA:tracrRNA complex, where 500 cpms of radiolabeled crRNA was spiked into the reaction. Cas9 or dCas9 binding to crRNA:tracrRNA complex was determined by dot-blot filter binding assays (see below). At concentrations above the $K_d$ value, binding is proportional to the amount of protein added and results in a straight line when plotting radioactivity versus protein. Once the Cas9 or dCas9 binding has saturated the crRNA:tracrRNA ligand, binding plateaus and is also a straight line. The value of x where the two lines intersect is equivalent to 0.5 µM of Cas9 or dCas9. To find this value, set the two linear equations equal to one another and algebraically solve for x.

Example 5—Dot-Blot Filter Binding Assays for Duplex Target Binding

For inhibitor binding by Cas9 RNP complexes, radiolabeled inhibitor (500 cpms/reaction) was combined with increasing concentrations of a pre-assembled dCas9- tracrRNA complex, with or without crRNA bound, in a final reaction of 40 μL 1× cleavage buffer (20 mM Tris-HCl, pH 7.5, 100 mM KCl, 5% glycerol, 1 mM DTT, 0.5 mM EDTA, 2 mM $MgCl_2$) and 0.1 mg/mL of purified yeast tRNA. After incubation at 37° C. for 15 min, reactions were vacuum filtered over nitrocellulose membrane (Protran Premium NC, Amersham) using a 96-well dot blot apparatus. Wells were washed twice with 200 μL of 1× cleavage buffer. Membrane was then removed and washed with 1×PBS solution and air dried at RT. Binding of radioactive crRNA was then visualized by phosphorimager. Spots were quantified with ImageQuant software, plotted in Prism (Graph-Pad) and fit to a one-site binding hyperbola equation. Error bars for all quantified data represent experimental replicates, not technical replicates. Sample size was selected based on the expectation that 3 or more replicates will be representative of typical in vitro assay conditions.

Example 6—In Vitro Cas9 Cleavage Activity Assays

PCR-amplified DNA (1 kb fragment) containing the EGFP target gene was purified by phenol-chloroform extraction and ethanol precipitation. The Cas9 pre-RNP complex was assembled (typical final concentrations: 0.5 μM Cas9, 0.25 μM tracrRNA) in a 1× cleavage buffer supplemented with 0.1 mg/mL of purified yeast tRNA. The concentration of tracrRNA was purposely set as the limiting component of the RNP complex and used to predict final RNP concentration. The crRNA (0.3 μM final), any inhibitors, and target DNA (100 ng) were spotted into tubes. The Cas9 pre-RNP was then added to these tubes to begin the reaction. A small molar excess of Cas9 and crRNA ensures complete assembly of tracrRNA into RNP complexes. Inhibitor molecules were added at the final concentrations indicated in each experiment.

Standard reaction conditions were 37° C. for 10 min or 1 h in a final reaction volume of 40 μL. The reaction was stopped by the addition of 10 vol of 2% $LiClO_4$ in acetone and precipitated for >1 h at −20° C. Precipitated reactions were centrifuged and washed with acetone, air dried, and re-suspended in 1× loading dye (10% glycerol, 1×TBE, orange G dye) containing 10 μg of Proteinase K. For time-course experiments, reactions were stopped at specified time points by the addition of 2% $LiClO_4$ in acetone and placed on ice, then worked-up the same as other samples. After dissolving the pellet, the reactions were incubated at RT for 20 mM, then resolved on TBE-buffered 1% agarose gels. Gels were stained with ethidium bromide and visualized by UV imager.

The fraction of target cleaved was quantified using ImageJ software. The band intensity for the cleavage product band was divided by the combined intensity of cleavage product and uncut substrate bands and reported as fraction cleaved (i.e. "cut"/"cut+uncut"). Time course cleavage assay results were plotted using Prism (Graphpad) software and fit to a one-site binding hyperbola by non-linear regression. Error bars for all quantified data represent experimental replicates, not technical replicates. Samples size was selected based on the expectation that 3 or more replicates will be representative of typical in vitro assay conditions.

Example 7—Inhibition of Cell-Based Editing

HEK cells expressing EGFP and Spy Cas9 were transfected with 20 pmols of sgRNA or crRNA:tracrRNA complex using RNAiMAX following the manufacturer's recommended protocol. Inhibitors were included at the same molar concentration as guide RNAs (20 pmols) and co-transfected. After 12 h, Opti-MEM was replaced with full media plus 1× Penicillin-Streptomycin solution and cells were grown for a total of 48 h post-transfection. Genomic DNA (gDNA) was harvested by washing the cells and dissolving them in a Tris-buffered (20 mM, pH 7.4) sarkosyl (0.1%) solution at 60° C. in the presence of Proteinase K (40 μg/mL). After 2.5 h, cell lysate was collected and precipitated with 200 mM NaCl and 75% ethanol. Genomic DNA is washed with 70% ethanol, dried, and quantified by qPCR using GAPDH genomic DNA primers. Based on a previously determined standard curve, approximately 100 ng of gDNA is amplified for 30 cycles using Phusion polymerase and primers that lie 200 bases upstream and 500 bases downstream of the expected cut site. PCR reactions are purified by mini-column purification and sent for Sanger sequencing using the forward Phusion primer. The Sanger sequencing results are then analyzed by TIDE analysis to predict the % editing efficiency.

Example 8—Inhibition of CRISPR Enzyme Activity

The methods used were those as described in Examples 1-7, unless indicated otherwise.

The studies described above have resulted in a strategy and in the production of prototype molecules that provide for inhibition of CRISPR effector enzymes. The molecules were prepared using synthetic and chemically-modified oligonucleotides. A key feature of the molecules presented herein is high specificity and affinity for the CRISPR enzyme. This is achieved through designing the molecules to include oligonucleotide sequences that bind CRISPR enzymes at multiple points of contact. These oligonucleotides and their modifications are compiled in FIG. 1. At least three points of contact of the oligonucleotide with the CRISPR enzyme have been identified that establish high affinity and target specificity. These points of contact involve interaction with the protospacer adjacent motif (PAM)-interaction (PI) domain of the Cas protein (i.e. Cas9), pairing to the guide sequence of the crRNA or single-guide RNA (sgRNA), and pairing to the repeat region of the trans-activating crRNA (tracrRNA, SEQ ID NO:9) or the equivalent position of a sgRNA (FIG. 2). The anti-CRISPR artificial DNA nucleic acid constructs possess one or more modules that interact with at least one or more points of contact on the CRISPR enzyme. Other points of contact with Cas enzymes or their RNA guides, such as regions that allosterically regulate enzyme conformation or activity, may later be characterized that can also be targeted to modulate binding and inhibition by nucleic acids.

While some inhibitors may function with only a single point of contact, the most effective inhibitors employ modules that engage two or more points of contact to an individual molecule. Additional modules may be added to further improve other pharmacologic properties of the inhibitors, including tissue delivery or cellular localization. Modules may also include nucleic acids that have been in vitro evolved and selected, such as aptamers, to specifically interact with points of contact on Cas proteins.

Figure 4A:
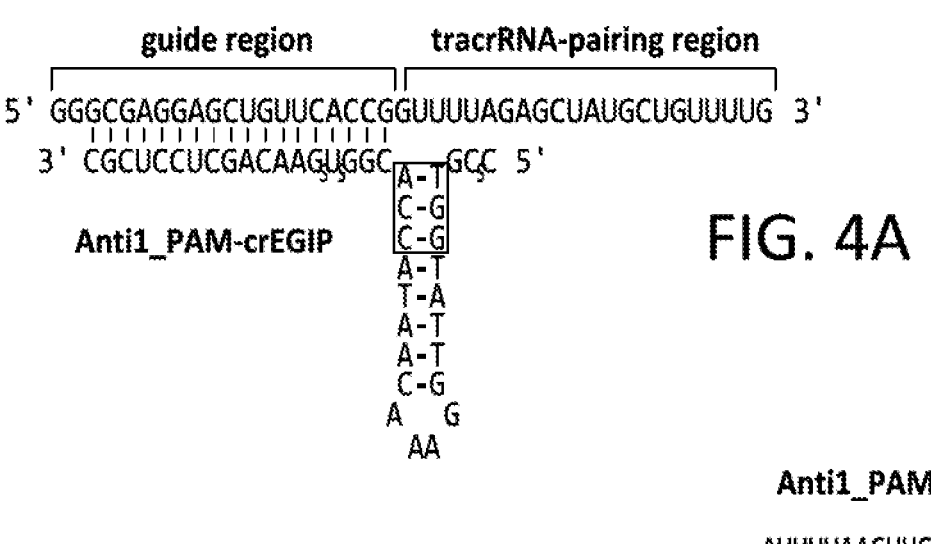
Figure 4B:
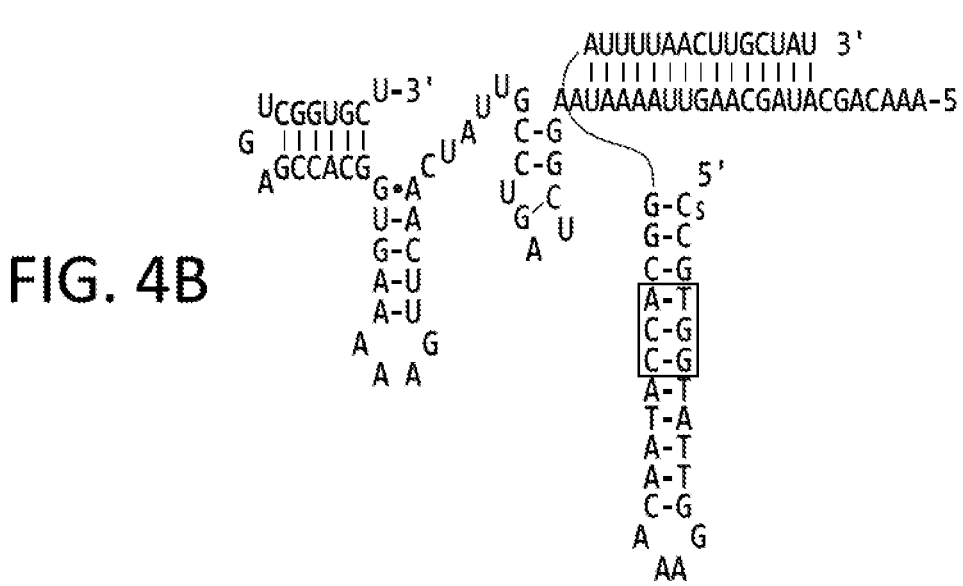
Figure 4C:
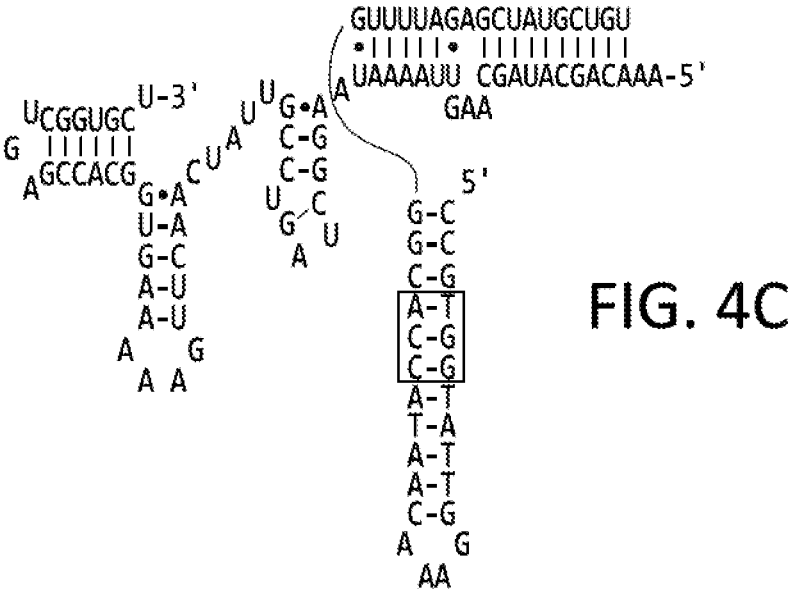
Figure 4D:
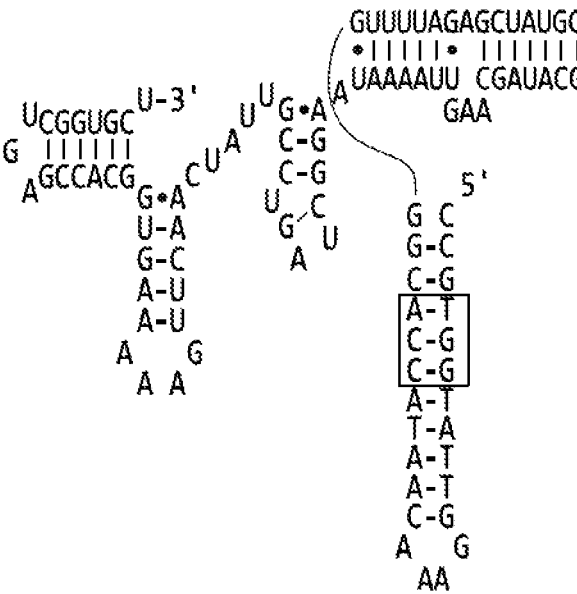
Figure 4E:
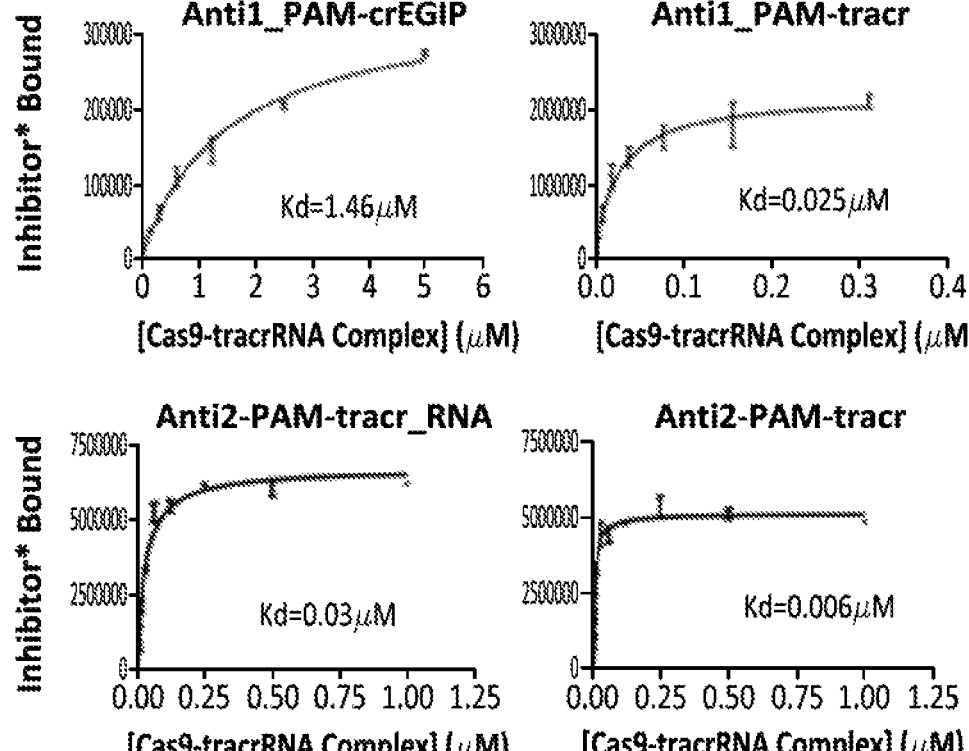

Several different prototype molecules were tested as proof-of-principle based on the general design strategy described above. Inhibitor candidates targeting each point of contact were initially designed and tested against *Streptococcus pyogenes* (Spy) Cas9 with or without its tracrRNA or crRNA guides (FIGS. 3A-3D). These were generally found to have low to moderate binding affinity (FIG. 3E). Targeting only the guide sequence resulted in the weakest binding (16 μM), whereas targeting the PI domain of Cas9 with Anti1-PAM resulted in a moderately high binding affinity of 0.15 μM, illustrating the strong interaction with target DNA during substrate searching by Spy Cas9. Further adjustments in design, such as chemical modification, may improve single-contact-point (SCP) inhibitors. However, multiple-contact-point (MCP) inhibitors combining two binding modules generally enhanced binding affinity (FIG. 4). While an anti-guide and anti-tracr combination (Anti1_PAM-crE-GIP, SEQ ID NO: 8) did not perform particularly well ($K_d$=1.46 μM) (FIG. 4E), combining an anti-PAM and anti-tracr module together (Anti1_PAM-tracr, SEQ ID NO: 9) resulted in a strong binding affinity of 25 nM. Designing the anti-tracr module to mimic the natural crRNA motif (Anti2_PAM-tracr RNA, SEQ ID NO: 10) resulted in a binding affinity of 30 nM. This same design was modified so that the anti-tracr module was converted from RNA to 2'-O-methyl, which resulted in a very high binding affinity of 6 nM (FIG. 4E).

These MCP nucleic acid inhibitors can further be optimized by systematically modifying each module. For example, altering the anti-tracr module's chemical nature (other RNA analogs besides 2'-O-methyl-RNA, such as 2'F-RNA. 2'-methoxyethyl (MOE) RNA, locked nucleic acid (LNA), and other bicyclo or bridged nucleic acids (BNAs)), altering the anti-PAM module sequence, size and chemical nature (DNA analogs, such as arabinonucleic acid (ANA), 2'F-ANA, alpha-L-LNA, and phosphorothioate (PS) DNA), adding modifications to improve nuclease resistance or cellular uptake (such as PS linkages or conjugates like cholesterol and small molecules) and adjusting the length and chemical nature of the linker(s) connecting binding modules.

One molecule with moderate/high binding activity was selected, Anti1_PAM-tracr (SEQ ID NO: 11), and its ability to block assembly and cleavage activity of dual RNA-guided (crRNA+tracrRNA) Spy Cas9 was tested. Activity was significantly reduced at early time points and never reached completion after 1 h of incubation when the inhibitor was at a 3-fold molar excess (FIG. 5A).

Based on these results, inhibitors with modules that simultaneously engage the protein and RNA guide component of CRISPR effector enzymes and RNP complexes will be highly effective. They take advantage of multiple, distinct modes of interaction, such as nucleic acid-protein binding and nucleic acid hybridization. Chemical modification with the correct chemistries in anti-tracr or anti-CRISPR modules also significantly improves the performance of inhibitors. Making base-pairing essentially irreversible under physiological conditions with strong $T_m$-stabilizing modifications, like bridged or bicyclo nucleic acids (BNAs such as LNA), could generate potent inhibitors. To test this idea, Anti_PAM-tracr inhibitor molecules were created where the anti-tracr module was chemically modified to 2'-F-RNA (Anti1_cr1, SEQ ID NO: 12) or 2'-F-RNA containing evenly spaced LNA nucleotides (Anti1_cr2, SEQ ID NO: 13). These inhibitor molecules both performed better than the control Anti1_PAM-tracr inhibitor when blocking enzyme activity in vitro (FIG. 5B). Thus, these results demonstrate that chemical modification schemes will help lead to molecules with potential for effective biotechnology and therapeutic applications.

The activity of a model inhibitor, Anti1_PAM-tracr, was also tested inside of cells. The crRNA and tracrRNA guides, or a sgRNA, targeting EGFP were co-transfected into HEK cells with equal molar amounts of Anti1_PAM-tracr. The HEK cells stably express EGFP and Spy Cas9. After 48 h of incubation to allow editing, a decrease in EGFP editing efficiency, determined by TIDE analysis, was observed for both dual RNA-guided and single RNA-guided Cas9 (FIG. 5C). Thus, the nucleic acid inhibitors described in this invention have successfully demonstrated the ability to inhibit enzyme activity inside of cells.

In summary, these studies demonstrate the design of a new strategy to inhibit CRISPR effector enzymes. This strategy is based on specifically designed nucleic acid constructs that possess the ability to make multiple points of contact with the CRISPR enzyme, and the resulting mimicry of natural guide RNA or target DNA binding to the effector enzyme. This strategy may extend to novel nucleic acids that are designed or in vitro evolved and selected (i.e. aptamers) to interact with CRISPR proteins at new points of contact in addition to those demonstrated here. This strategy should conceivably extend to all nucleic acid-guided CRISPR effector enzymes, including Cas12a (Cpf1), multi-component CRISPR enzymes (for example the Cascade complex) and enzymes from other CRISPR classes and enzyme types. Certain designs may also prove effective in inhibiting the DNA binding activity, and therefore function, of catalytically inactive CRISPR effectors, such as 'dead' Cas9.

Example 9—Anti1_PAM-tracr FL, Linker Length

The present example presents studies that include calculation of a binding affinity for one of the higher performing anti-CRISPR nucleic acids, Anti1_PAM-tracr_FL (FIG. 6), and characterization of the nature of the linker between anti-tracr and anti-PAM modules (FIG. 7 and FIG. 8). The binding affinity measured for Anti_PAM-tracr FL was 1.4+/−0.4 nM. This is the strongest binding affinity measured for a CRISPR inhibitor molecule to date.

Linkers of many lengths and composition are demonstrated here to be tolerated, and shorter linkers also appeared to be more effective. Linker lengths from 27 atom polyethylene glycol (PEG) linkers down to 3 atom PEG linkers were examined and measured binding affinity (FIG. 7). The linker was also replaced with a single thymine (T) DNA nucleotide or removed the linker altogether and fused the anti-tracr and anti-PAM modules together (they were synthesized as one contiguous oligonucleotide).

The linker composed of just a T nucleotide seemed to perform the best in cell-based genome editing assays (FIG. 8). Having no linker also resulted in efficient inhibition of editing. Thus, the linker can be composed of diverse lengths and chemistries, or even be removed, while still providing efficient inhibition and strong binding to Cas9.

Example 10—Lipid Transfection and Flow Cytometry

HEK 293T cells expressing both EGFP and SpCas9 were grown in Dulbecco's modified Eagle's medium with 1% non-essential amino acids, 5% Cosmic calf serum, 5% fetal bovine serum (FBS), and without antibiotics. Cells were reverse transfected (40,000 cells/well in a 96-well dish) with 5 pmols sgRNA in a final volume of 200 μL following the manufacturer's recommended protocol. Inhibitors were co-transfected with a sgRNA targeting EGFP at a 1:1 molar ratio. After 8 hours the media was replaced with full media, and the cells allowed to grow for 5 days with a fresh media change every 2 days. After 5 days, the cells were harvested and analyzed by flow cytometry.

Before flow cytometry, cells were harvested by trypsinization, washed with 1× PBS, and resuspended in 200 μL 1×PBS. Cells were counted on an Attune NXT flow cytometer (Thermo Fischer Scientific). 20,000 events were counted and analyzed using Attune® NxT Software. The cells were first gated based on forward and side scattering (FSC-A/SSC-A) to remove cell debris, and then gated to select single cells (FSC-H/FSC-A). Finally, cells were gated to select EGFP positive cells. The quadrant gate was based on the signal from non-EGFP expressing control cells. Untreated HEK293T cells expressing both SpCas9 and EGFP contained about 5% nonfluorescent cells. The average from six untreated replicates was used for background.

The examples set forth above are provided to give those of ordinary skill in the art a complete disclosure and description of how to make and use the embodiments of the methods for prediction of the selected modifications that may be made to a biomolecule of interest, and are not intended to limit the scope of what the inventors regard as the scope of the disclosure. Modifications of the above-described modes for carrying out the disclosure can be used by persons of skill in the art, and are intended to be within the scope of the following claims.

It is to be understood that the disclosure is not limited to particular methods or systems, which can, of course, vary. It is also to be understood that the terminology used herein is for the purpose of describing particular embodiments only, and is not intended to be limiting.

Research Tools:

The present invention also provides for the use of the various methods, constructs, and nucleic acid modification techniques described herein as a research tool for use in vitro or in cellulo (cell culture). For example, the nucleic acid constructs and fragments thereof, as well as the platform strategies described herein for CRISPR and other targeted strategies, may be used in devising methods and tolls useful for analyzing nucleic acid structure, either indirectly (e.g. by chemical probing, using electrophoresis, etc.) or directly (e.g. using fluorescence, NMR, or crystallography). Specific methods to prepare nucleic acid samples for structural analyses, as well as use of the herein described constructs and techniques for high through put screening of potential candidate molecules, is also provided.

In addition, the constructs and strategies provided herein may be employed as part of a method for further characterizing enzymes involved in nucleic acid biochemistry. By way of example, such processes may focus on CRISPR enzymes or other enzymes that act directly on DNA or RNA, or on proteins that interact with such species. Nucleic acids with inherent enzymatic activity are of particular interest, as are their involvement in multi-protein complexes.

In yet other applications, the nucleic acid constructs, methods and strategies disclosed herein may be employed in methods for the analysis of protein-nucleic acid interactions including ChIP, footprinting, interference, cross-linking, fluorescence techniques, one- and tri-hybrid strategies, in vivo methods, and analyses of mutants.

A number of embodiments of the disclosure have been described. Nevertheless, it will be understood that various modifications may be made without departing from the spirit and scope of the present disclosure. Accordingly, other embodiments are within the scope of the following claims.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

```
                        SEQUENCE LISTING

SEQ ID NO: 1
LENGTH: 23
TYPE: DNA
ORGANISM: Artificial Sequence
OTHER INFORMATION: Polynucleotide that Interacts with a PI Domain of a
Cas Protein
CCGTGGTATT GGAAACAATA CCA                    23

SEQ ID NO: 2
LENGTH: 26
TYPE: DNA
ORGANISM: Artificial Sequence
OTHER INFORMATION: Polynucleotide that Interacts with a PI Domain of a
Cas Protein
CCGTGGTATT GGAAACAATA CCACGG                 26

SEQ ID NO: 3
LENGTH: 17
TYPE: RNA
ORGANISM: Artificial Sequence
OTHER INFORMATION: Polynucleotide that Interacts with a Repeat Region of
a tracrRNA or an Equivalent Position of a Single-Guide RNA
UUAUUUUAAC UUGCUAU                           17

SEQ ID NO: 4
LENGTH: 15
TYPE: RNA
ORGANISM: Artificial Sequence
OTHER INFORMATION: Polynucleotide that Interacts with a Repeat Region of
a tracrRNA or an Equivalent Position of a Single-Guide RNA
AUUUUAACUU GCUAU                             15
```

-continued

SEQUENCE LISTING

```
SEQ ID NO: 5
LENGTH: 18
TYPE: RNA
ORGANISM: Artificial Sequence
OTHER INFORMATION: Polynucleotide that Interacts with a Repeat Region of
a tracrRNA or an Equivalent Position of a Single-Guide RNA
GUUUUAGAGC UAUGCUGU                                18

SEQ ID NO: 6
LENGTH: 15
TYPE: RNA
ORGANISM: Artificial Sequence
OTHER INFORMATION: Polynucleotide that Interacts with a Repeat Region of
a tracrRNA or an Equivalent Position of a Single-Guide RNA
AUUTUAACUT GCUAU                                   15

SEQ ID NO: 7
LENGTH: 18
TYPE: RNA
ORGANISM: Artificial Sequence
OTHER INFORMATION: Polynucleotide that Interacts with a Guide Sequence
of a crRNA or an Equivalent Position of a Single-Guide RNA
CGGUGAACAG CUCCUCGC                                18
```

REFERENCES

The following references are specifically incorporated herein in their entirety.

Ausubel et al. (2002) Short Protocols in Molecular Biology, 5th ed., Current Protocols.

Elhai and Wolk. (1988) Methods in Enzymology 167, 747-754.

Sambrook and Russel. (2001) Molecular Cloning: A Laboratory Manual, 3rd ed., Cold Spring Harbor Laboratory Press.

Sambrook and Russel. (2006) Condensed Protocols from Molecular Cloning: A Laboratory Manual, Cold Spring Harbor Laboratory Press.

Barkau et al., (2019) Nucleic Acid Therapeutics, 29 (3): 136-147.

What is claimed is:

1. A CRISPR inhibitor molecule comprising an artificial nucleic acid construct having a first polynucleotide, a second polynucleotide, and a linker molecule, wherein:

the first polynucleotide is a polynucleotide that interacts with a protospacer adjacent motif-interaction domain of a CRISPR-associated protein and comprises a sequence selected from the group consisting of:

SEQ ID NO: 1 or a sequence at least 95% identical thereto; and

SEQ ID NO: 2 or a sequence at least 95% identical thereto;

the second polynucleotide is a polynucleotide that interacts with a repeat region of a tracrRNA or an equivalent position of a single-guide RNA and comprises a sequence selected from the group consisting of:

SEQ ID NO: 4 or a sequence at least 95% identical thereto;

SEQ ID NO: 5 or a sequence at least 95% identical thereto; and

SEQ ID NO: 6 or a sequence at least 95% identical thereto;

and wherein the linker molecule is operably connected to said first polynucleotide and operably connected to said second polynucleotide.

2. The CRISPR inhibitor molecule of claim 1, wherein said second polynucleotide further comprises a polynucleotide that interacts with a guide sequence of a crRNA or an equivalent position of a single-guide RNA.

3. The CRISPR inhibitor molecule of claim 2, wherein said polynucleotide that interacts with said guide sequence of said crRNA or said equivalent position of said single-guide RNA comprises:

a 2'-deoxyribonucleotide;

a 2'-deoxyribonucleotide analog;

a ribonucleotide;

a ribonucleotide analog; or a combination thereof.

4. The CRISPR inhibitor molecule of claim 2, wherein said polynucleotide that interacts with said guide sequence of said crRNA or said equivalent position of said single-guide RNA comprises at least one internucleotide linkage selected from the group consisting of phosphodiester, phosphorothioate, phosphotriester, phosphorodithioate, boranophosphate, Rp- and/or Sp-phosphorothioate, 3' thioformacetal, methylene, amide, methylphosphonate, phosphoramidate and any combination thereof.

5. The CRISPR inhibitor molecule of claim 2, wherein said polynucleotide that interacts with said guide sequence of said crRNA or said equivalent position of said single-guide RNA comprises SEQ ID NO: Z or a sequence at least 95% identical thereto.

6. The CRISPR inhibitor molecule of claim 1, wherein said polynucleotide that interacts with said repeat region of said tracrRNA or said equivalent position of said single-guide RNA comprises:

a 2'-deoxyribonucleotide;

a 2'-deoxyribonucleotide analog;

a ribonucleotide;

a ribonucleotide analog; or a combination thereof.

7. The CRISPR inhibitor molecule of claim 1, wherein said polynucleotide that interacts with said repeat region of said tracrRNA or said equivalent position of said single-guide RNA comprises at least one internucleotide linkage selected from the group consisting of phosphodiester, phosphorothioate, phosphotriester, phosphorodithioate, boranophosphate, Rp- and/or Sp-phosphorothioate, 3' thioformacetal, methylene, amide, methylphosphonate, phosphoramidate and any combination thereof.

8. The CRISPR inhibitor molecule of claim 1, wherein said linker molecule comprises polyethylene glycol.

9. The CRISPR inhibitor molecule of claim 1, wherein said linker molecule comprises one or more nucleic acids, wherein a linker molecule having more than one nucleic acid may comprise a single stranded oligonucleotide having a spacer functionality within the artificial nucleic acid construct.

10. The CRISPR inhibitor molecule of claim 1, wherein the first polynucleotide comprises:
   a 2'-deoxyribonucleotides;
   a 2'-deoxyribonucleotide analog;
   a ribonucleotide;
   a ribonucleotide analog; or
   any combination thereof.

11. The CRISPR inhibitor molecule of claim 1, wherein the first polynucleotide comprises at least one internucleotide linkage selected from the group consisting of phosphodiester, phosphorothioate, phosphotriester, phosphorodithioate, boranophosphate, Rp- and/or Sp-phosphorothioate, 3' thioformacetal, methylene, amide, methylphosphonate, phosphoramidate and any combination thereof.

* * * * *